(12) United States Patent
Song et al.

(10) Patent No.: US 12,198,679 B2
(45) Date of Patent: *Jan. 14, 2025

(54) METHOD OF OBTAINING HIGH ACCURACY URINATION INFORMATION

(71) Applicant: DAIN TECHNOLOGY, INC., Seoul (KR)

(72) Inventors: Jee Young Song, Seoul (KR); Kyeong Yeon Doo, Seoul (KR); Ji Young Jung, Gyeonggi-do (KR); Daeyeon Kim, Seoul (KR)

(73) Assignee: DAIN TECHNOLOGY, INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/362,436

(22) Filed: Jul. 31, 2023

(65) Prior Publication Data

US 2023/0377566 A1    Nov. 23, 2023

Related U.S. Application Data

(63) Continuation of application No. 17/891,630, filed on Aug. 19, 2022, now Pat. No. 11,763,802, which is a
(Continued)

(30) Foreign Application Priority Data

Mar. 2, 2021    (KR) .................... 10-2021-0027771

(51) Int. Cl.
*G10L 15/08*    (2006.01)
*G06N 3/02*    (2006.01)
*G10L 15/06*    (2013.01)

(52) U.S. Cl.
CPC ............... *G10L 15/08* (2013.01); *G06N 3/02* (2013.01); *G10L 15/063* (2013.01)

(58) Field of Classification Search
CPC ....... G10L 15/08; G10L 15/063; G10L 25/30; G10L 25/51; G06N 3/02; A61B 5/00; A61B 5/20; A61B 5/208
See application file for complete search history.

(56) References Cited

U.S. PATENT DOCUMENTS 11,207,012 B2 *  12/2021  Belotserkovsky ..... A61B 5/202
2009/0062644 A1 *  3/2009  McMorrow .............. A61B 8/08
                                                                600/437
(Continued)

FOREIGN PATENT DOCUMENTS

KR         10-2013418      8/2019
KR     10-2020-0002093 A   1/2020
(Continued)

OTHER PUBLICATIONS

P. Hurtík, et al. "Automatic Diagnosis of Voiding Dysfunction From Sound Signal," 2015 IEEE Symposium Series on Computational Intelligence, 2015, pp. 1331-1336.
(Continued)

*Primary Examiner* — Michael Colucci
(74) *Attorney, Agent, or Firm* — Reed Smith LLP

(57) ABSTRACT

A method of obtaining high accuracy urination information is proposed. There may be provided the method of obtaining the urination information, wherein sound data is divided into a plurality of windows, segmented target data corresponding to respective windows is obtained from the sound data, segmented classification data classifying urination sections or non-urination sections and segmented urine flow rate data are obtained by using the obtained segmented target data, and urination data is obtained by using the obtained segmented classification data and the segmented urine flow rate data.

17 Claims, 26 Drawing Sheets

Related U.S. Application Data continuation of application No. PCT/KR2022/002956, filed on Mar. 2, 2022.

(56) References Cited

U.S. PATENT DOCUMENTS

| | | | |
|---|---|---|---|
| 2011/0029603 A1 | 2/2011 | Brohan et al. | |
| 2014/0018702 A1* | 1/2014 | Belotserkovsky | A61B 5/208 |
| | | | 600/584 |
| 2016/0058412 A1* | 3/2016 | Yoshimura | A61B 8/5207 |
| | | | 600/438 |
| 2018/0163388 A1* | 6/2018 | Staton | A61B 10/007 |
| 2020/0124587 A1* | 4/2020 | Dechev | G01N 21/255 |
| 2020/0394781 A1* | 12/2020 | Hall | G06V 10/82 |
| 2021/0275073 A1* | 9/2021 | Korkor, II | G10L 25/66 |
| 2022/0074918 A1* | 3/2022 | Hall | G01N 33/4833 |

FOREIGN PATENT DOCUMENTS

| | | |
|---|---|---|
| KR | 10-2198846 | 1/2021 |
| KR | 10-2247730 | 5/2021 |
| WO | 2012121772 | 9/2012 |

OTHER PUBLICATIONS

Jin, J., et al. Development of a Flowmeter Using Vibration Interaction between Gauge Plate and External Flow Analyzed by LSTM. Sensors 2020, 20, 5922.
International Search Report cited in PCT/KR2022/002956, Jun. 9, 2022, 3 pages.
Written Opinion cited in PCT/KR2022/002956, Jun. 9, 2022, 3 pages.

* cited by examiner

METHOD OF OBTAINING HIGH ACCURACY URINATION INFORMATION

CROSS-REFERENCE TO RELATED APPLICATIONS

This application is a Continuation of U.S. application Ser. No. 17/891,630 filed Aug. 19, 2022, which is a Continuation of PCT International Application No. PCT/KR2022/002956, filed Mar. 2, 2022, which claims priority to Korean Patent Application No. 10-2021-0027771, filed Mar. 2, 2021, the entire contents of each of which are hereby expressly incorporated by reference.

TECHNICAL FIELD

The present specification relates to a method of obtaining high accuracy urination information and, more particularly, to a method of extracting urination information from urination-related sound data recorded by using a urination/non-urination section classification model and a urine flow rate prediction model.

BACKGROUND ART

Sound generated from a person's body has been used as important information in confirming a person's health status or whether a person has a disease. In particular, the sound generated in a urination process of the person may include important information for diagnosing a person's urination function, so study on a method of obtaining urination information by analyzing urination sound is continuously being conducted. Specifically, a urine flow rate or a urine volume of the person may be predicted by analyzing sound data obtained by recording sound in the urination process of the person.

Meanwhile, the sound generated in the urination process of the person may include various sounds generated due to a surrounding environment in addition to the urination-related sound. The sound caused by the surrounding environment may be included in a urination section or a non-urination section in the urination process. In particular, in a case where the sound caused by the surrounding environment is included in the non-urination section and reflected in the sound data, there is a problem in that an analysis result is not accurate.

Therefore, in order to obtain more accurate urination information, a method of analyzing the sound data for the urination process is required in consideration of the case where the sound caused by the surrounding environment is included in the non-urination section.

DISCLOSURE

Technical Problem

An objective of the present specification to solve one problem is to provide a method of obtaining urination information, wherein high accuracy urination information is obtained from sound data obtained by recording sound in the urination process of a person.

Another objective of the present specification to solve one problem is to provide a method of obtaining urination information by using a model for classifying the urination process into urination sections and non-urination sections and a model for predicting a urine flow rate in the urination process.

Yet another objective of the present specification to solve one problem is to provide a method of first determining whether or not a urination process is occurring for collected sound data and then performing urine flow rate prediction.

The problem to be solved in this specification is not limited to the above-mentioned problems, and the problems not mentioned will be clearly understood by those skilled in the art to which the present disclosure belongs from the present specification and accompanying drawings.

Technical Solution

According to one embodiment of the present specification, a method of obtaining high accuracy urination information may be provided, the method of obtaining urination information comprises: obtaining sound data, wherein the sound data have a starting point and an ending point; obtaining first to m-th segmented target data corresponding to m windows from the sound data, wherein each of the m windows has a predetermined time period, and is sequentially determined between the starting point and the ending point, consecutive windows among the m windows partially overlap each other, and the m is a natural number greater than or equal to 2; obtaining first to m-th segmented classification data by inputting the first to m-th segmented target data into a pre-trained urination/non-urination classification model, wherein the urination/non-urination classification model is trained to output data comprising at least one value for classifying a urination section or a non-urination section when first data matrix inputted; obtaining first to n-th segmented target data corresponding to n windows from the sound data, wherein each of the n windows has a predetermined time period, and is sequentially determined between the starting point and the ending point, consecutive windows among the n windows partially overlap each other, and the n is the natural number greater than or equal to 2; obtaining first to n-th segmented urine flow rate data by inputting the first to n-th segmented target data into a pre-trained urine flow rate prediction model, wherein the urine flow rate prediction model is trained to output data comprising at least one value for urine flow rate when second data matrix inputted; and obtaining urination data using at least the first to m-th segmented classification data and the first to n-th segmented urine flow rate data.

According to another embodiment of the present specification, a method of obtaining high accuracy urination information may be provided, the method of obtaining urination information comprises: obtaining sound data by sampling a sound signal obtained by recording a urination process through an external device, wherein the sound data have a starting point and ending point; obtaining first to n-th segmented target data corresponding to first to n-th windows from the sound data, wherein each of the first to n-th windows has a predetermined time period, and is sequentially determined between the starting point and the ending point, and then is a natural number greater than or equal to 2; obtaining first to m-th segmented classification data by inputting at least a part of the first to n-th segmented target data into a pre-trained urination/non-urination classification model, wherein the urination/non-urination classification model is trained to output data comprising at least one value for classifying a urination section or a non-urination section when first data matrix inputted, and the m is the natural number greater than or equal to 2 and less than or equal to the n; obtaining first to n-th segmented urine flow rate data by inputting the first to n-th segmented target data into a pre-trained urine flow rate prediction model, wherein the urine flow rate prediction model is trained to output data including at least one value for urine flow rate when second data matrix inputted; and obtaining urination data using at least the first to m-th segmented classification data and the first to n-th segmented urine flow rate data.

The problem solutions of the present specification are not limited to the above-described problem solutions, and solutions that are not mentioned may be understood clearly to those skilled in the art to which the present disclosure belongs from the present specification and the accompanying drawings.

Advantageous Effects

According to an embodiment of the present specification, a result of classifying the urination process into the urination sections and the non-urination sections and a result of predicting the urine flow rate in the urination process are used together, whereby a prediction result of a highly accurate urine flow rate for the urination process may be obtained.

According to an embodiment of the present specification, data obtained by classifying the urination process into the urination sections and the non-urination sections is used, whereby urine flow rate data in the non-urination section is prevented from being included in a result of predicting the urine flow rate of the urination process.

According to an embodiment of the present specification, whether or not a urination process is occurring is by first determined prior to predicting a urinary flow rate, whereby unnecessary data analysis may be prevented in advance.

The effects according to the present specification are not limited to the above-described effects, and effects not mentioned herein may be clearly understood by those skilled in the art to which the present disclosure belongs from the present specification and accompanying drawings.

Figure 1:
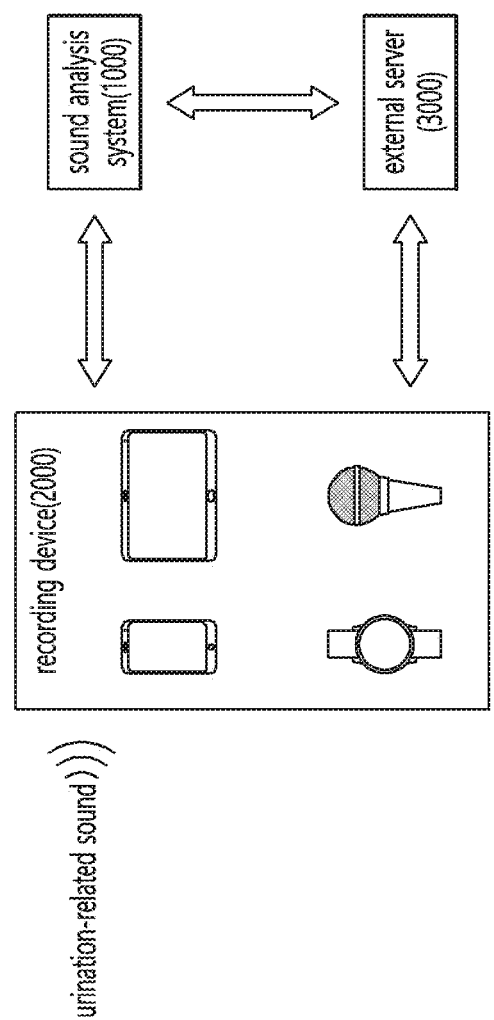
FIG. 1 is a view illustrating an environment for analyzing urination information according to an exemplary embodiment of the present specification.

According to an embodiment of the present specification, a method of obtaining high accuracy urination information may be provided, and the method of obtaining urination information may include obtaining sound data, wherein the sound data have a starting point and an ending point; obtaining first to m-th segmented target data corresponding to m windows from the sound data, wherein each of the m windows has a predetermined time period, and is sequentially determined between the starting point and the ending point, consecutive windows among the m windows partially overlap each other, and the m is a natural number greater than or equal to 2; obtaining first to m-th segmented classification data by inputting the first to m-th segmented target data into a pre-trained urination/non-urination classification model, wherein the urination/non-urination classification model is trained to output data comprising at least one value for classifying a urination section or a non-urination section when first data matrix inputted; obtaining first to n-th segmented target data corresponding to n windows from the sound data, wherein each of the n windows has a predetermined time period, and is sequentially determined between the starting point and the ending point, consecutive windows among the n windows partially overlap each other, and the n is the natural number greater than or equal to 2; obtaining first to n-th segmented urine flow rate data by inputting the first to n-th segmented target data into a pre-trained urine flow rate prediction model, wherein the urine flow rate prediction model is trained to output data comprising at least one value for urine flow rate when second data matrix inputted; and obtaining urination data using at least the first to m-th segmented classification data and the first to n-th segmented urine flow rate data.

An overlapping degree of the consecutive windows among the m windows may be different from an overlapping degree of consecutive windows among then windows.

The overlapping degree of the consecutive windows among the m windows may be less than the overlapping degree of consecutive windows among then windows.

Each of the first to m-th pieces segmented target data and the first to n-th segmented target data may include a feature value extracted from at least a part of the sound data.

The obtaining the first to m-th segmented target data may include transforming the sound data to spectrogram data; and obtaining the first to m-th segmented target data corresponding to the first to m-th windows from the spectrogram data.

The obtaining the first to m-th segmented target data may include obtaining first to m-th segmented sound data corresponding to the first to m-th windows; and transforming each of the first to m-th segmented sound data to spectrogram data to obtain the first to m-th segmented target data.

The spectrogram data may be obtained by applying a Mel-filter.

The first to m-th segmented classification data may be obtained by sequentially inputting the first to m-th segmented target data into the urination/non-urination classification model, and the first to n-th segmented urine flow rate data may be obtained by sequentially inputting the first to n-th segmented target data into the urine flow rate prediction model.

The urination/non-urination classification model may include at least first input layer, first convolution layer, first hidden layer, and first output layer, and the urine flow rate prediction model may include at least second input layer, second convolution layer, second hidden layer, and second output layer.

A size of the first data matrix bay be equal to a size of the second data matrix.

The obtaining the urination data may include obtaining urination classification data using the first to m-th segmented classification data; obtaining candidate urine flow rate data using the first to n-th segmented urine flow rate data; and processing the candidate urine flow rate data using the urination classification data.

The urination data may be obtained by convolution operating the urination classification data and the candidate urine flow rate data.

The method of obtaining urination information may further include determining whether a urination section exists for the sound data using the first to m-th segmented classification data after the obtaining the first to m-th segmented classification data, wherein when the urination section exists for the sound data, obtaining the first to n-th segmented target data from the sound data, obtaining the first to n-th segmented urine flow rate data by inputting the first to n-th segmented target data into the urine flow rate prediction model, and obtaining the urination data using at least the first to m-th segmented classification data and the first to n-th segmented urine flow rate data may be performed.

According to another embodiment of the present specification, a method of obtaining high accuracy urination information may be provided, and the method of obtaining urination information may include obtaining sound data by sampling a sound signal obtained by recording a urination process through an external device, wherein the sound data have a starting point and ending point; obtaining first to n-th segmented target data corresponding to first to n-th windows from the sound data, wherein each of the first to n-th windows has a predetermined time period, and is sequentially determined between the starting point and the ending point, and then is a natural number greater than or equal to 2; obtaining first to m-th segmented classification data by inputting at least a part of the first to n-th segmented target data into a pre-trained urination/non-urination classification model, wherein the urination/non-urination classification model is trained to output data comprising at least one value for classifying a urination section or a non-urination section when first data matrix inputted, and the m is the natural number greater than or equal to 2 and less than or equal to the n; obtaining first to n-th segmented urine flow rate data by inputting the first to n-th segmented target data into a pre-trained urine flow rate prediction model, wherein the urine flow rate prediction model is trained to output data including at least one value for urine flow rate when second data matrix inputted; and obtaining urination data using at least the first to m-th segmented classification data and the first to n-th segmented urine flow rate data.

The two consecutive windows among the first to n-th windows may overlap.

The two consecutive windows among the first to n-th windows may not overlap each other, and them may be equal to then.

Each of the first to n-th segmented target data may include a feature value extracted from at least a part of the sound data.

The obtaining the first to n-th segmented target data may include transforming the sound data to spectrogram data; and obtaining the first to n-th segmented target data corresponding to the first to n-th windows from the spectrogram data.

The obtaining the first to n-th segmented target data may include obtaining first to n-th segmented sound data corresponding to the first to n-th windows; and transforming each of the first to n-th segmented sound data to spectrogram data to obtain the first to n-th segmented target data.

The spectrogram data may be Mel-spectrogram data.

The first to m-th segmented classification data may be obtained by sequentially inputting m segmented target data corresponding to m windows that do not overlap each other among the first to n-th windows into the urination/non-urination classification model, and the first to n-th segmented urine flow rate data may be obtained by sequentially inputting the first to n-th segmented target data into the urine flow rate prediction model.

The urination/non-urination classification model may include at least first input layer, first convolution layer, first hidden layer, and first output layer, and the urine flow rate prediction model may include at least second input layer, second convolution layer, second hidden layer, and second output layer, wherein a data form input to the first input layer may be same as a data form input to the second input layer.

A size of the first data matrix may be equal to a size of the second data matrix.

The obtaining the urination data may include obtaining urination classification data using the first to m-th segmented classification data; obtaining candidate urine flow rate data using the first to n-th segmented urine flow rate data; and processing the candidate urine flow rate data using the urination classification data.

The urination data may be obtained by convolution operating the urination classification data and the candidate urine flow rate data.

According to another embodiment of the present specification, a method of correcting data may be provided, the method may include obtaining actual measurement data group for a plurality of individuals in a data collection period, wherein the actual measurement data group includes at least first actual measurement data including urine volume measurement value of first individual and second actual measurement data including urine volume measurement data of second individual; obtaining prediction data group for urination process of the plurality of individuals in the data collection period, wherein the prediction data group includes first prediction data including urine volume prediction value of the first individual and second prediction value including urine volume prediction value of the second individual, the urine volume prediction value of the first individual is generated from first sound data recorded in urination process of the first individual, and the urine volume prediction value of the second individual is generated from second sound data recorded in urination process of the second individual; obtaining compensation value using the actual measurement data group and the prediction data group; obtaining target prediction data for the urination process of target individual after the data collection period, wherein the target prediction data includes urine volume prediction value for the urination process of the target individual, and the urine volume prediction value of the target individual is generated from target sound data recorded in the urination process of the target individual; and correcting the target prediction data using the compensation value.

The obtaining compensation value may include generating data set group using the actual measurement data group and the prediction data group; and calculating the compensation value from the data set group using a regression analysis technique.

The data set group may include first data set generated by matching a representative value of the urine volume prediction values included in the first prediction data to a representative value of the urine volume measurement values included in the first actual measurement data.

The data set group may include first data set generated by matching a representative value of urine volume measurement values in second time period among urine volume measurement values on a plurality of days included in the second actual measurement data to a representative value of urine volume measurement values in first time period among urine volume measurement values of a plurality of days included in the first actual measurement data, and a length of the first time period may be equal to a length of the second time period.

The regression analysis technique may be a linear regression analysis technique, and the compensation value may be a slope of a function obtained by using the linear regression analysis.

In the calculating the compensation value from the data set group using the regression analysis technique, a value obtained from the first actual measurement data may be used as either an independent variable or a dependent variable, and a value obtained from the first prediction data may be used as either the independent variable or the dependent variable, and the compensation value may be a regression coefficient calculated through the regression analysis technique.

The obtaining the target prediction data may include generating target urine flow rate data for the urination process of the target individual using the target sound data, and calculating urine volume prediction value for the urination process of the target individual from the target urine flow rate data.

The obtaining the actual measurement data group and the obtaining the prediction data group may be performed simultaneously.

According to another embodiment of the present specification, a method of correcting data may be provided, the method may include obtaining actual measurement data reflecting urine volume measured in urination process of target individual in a first term, wherein the actual measurement data includes at least one urine volume measurement value; obtaining sound data group recorded in the urination process of the target individual in the first term, wherein the sound data group includes first sound data recorded in first urination process; obtaining prediction data using the sound data group, wherein the prediction data includes a urine volume prediction value calculated from the first sound to data; obtaining a compensation value using the actual measurement data and the prediction data; obtaining second sound data recorded in second urination process of the target individual in second term after the first term; calculating a target urine volume prediction value from the second sound data; and correcting the target urine volume prediction value using the compensation value.

The obtaining compensation value may use regression analysis technique, wherein a value obtained from the actual measurement data is used as either an independent variable or a dependent variable, and a value obtained from the prediction data is used as the other of the independent variable or the dependent variable, and the compensation value may be a regression coefficient calculated through the regression analysis technique.

The value obtained from the actual measurement data may be a urine volume measurement value corresponding to the first urination process in the first term, and the value obtained from the prediction data may be the urine volume prediction value calculated from the first sound data.

The calculating the target urine volume prediction value from the second sound data may include generating target urine flow rate data using the second sound data; and calculating the target urine volume prediction value from the target urine flow rate data.

According to another embodiment of the present specification, a method of correcting data may be provided, the method may include obtaining actual measurement data reflecting urine volume measured in urination process for target individual in a first term, wherein the actual measurement data includes a plurality of urine volume measurement value; obtaining sound data by recording the urination process of the target individual in a second term after the first term; obtaining urine volume prediction data using the sound data; and correcting the urine volume prediction data using a statistical value of the actual measurement data; wherein the statistical value is at least one of a mode value, a median value, an average value, a variance value, or a standard deviation value of the urine volume measurement values included in the actual measurement data.

The above-described objectives, features, and advantages of the present specification will become more apparent from the following detailed description in conjunction with the accompanying drawings. However, since the present specification may have various changes and may have various exemplary embodiments, specific exemplary embodiments will be exemplified in the drawings and described in detail below.

The same reference numbers throughout the specification indicate the same components, in principle. In addition, components having the same function within the scope of the same idea shown in the drawings of each exemplary embodiment will be described by using the same reference numerals, and a redundant description thereof will be omitted.

Numbers (e.g., first, second, etc.) used in a process of describing the present specification are only division symbols for dividing one component from other components.

In addition, suffix-like words "module" and "part/unit" for the components used in the following exemplary embodiments are given or mixed in consideration of only the ease of writing the specification, and do not have distinct meanings or roles by themselves.

Unless specifically stated or clear from the context, a term "about" or "around" in reference to a numerical value may be understood to mean a stated numerical value and a value up to +/−10% of the numerical value. The term "about" or "around" in reference to a numerical range may be understood to mean a range from a value 10% lower than a lower limit of the numerical range to a value 10% higher than an upper limit of the numerical range.

In the exemplary embodiments below, the singular forms are intended to include the plural forms as well, unless the context clearly indicates otherwise.

In the following exemplary embodiments, terms such as "comprise", "include", or "have" mean that a feature or a component described in the specification is present, and the possibility that one or more other features or components may be added is not precluded.

In the drawings, the size of the components may be exaggerated or reduced for convenience of description. For example, the size and thickness of each component shown in the drawings or views are arbitrarily represented for convenience of description, and the present disclosure is not necessarily limited to the illustrated drawings or views.

Where certain exemplary embodiments are otherwise implementable, a specific process order may be performed different from the described order. For example, two processes described in succession may be performed substantially and simultaneously, or may be performed in an order opposite to the described order.

In the following exemplary embodiments, when a film, a region, a component, and/or the like are connected to a target, this includes not only a case where the film, the region, and/or the component are directly connected to the target, but also a case where the film, the region, and/or the component are indirectly connected to the target by means of another film, another region, and/or another component that are interposed therebetween.

For example, in the present specification, when it is said that a film, a region, a component, and/or the like are electrically connected to a target, this includes not only a case where the film, the region, the component, and/or the like are directly and electrically connected to the target, but also a case where the film, the region, the component, and/or the like are indirectly and electrically connected to the target by means of another film, another region, another component, and/or the like that are interposed therebetween.

The present specification relates to a method of obtaining high accuracy urination information and, more particularly, to a method of obtaining urination information, wherein sound data is obtained by recording sound in a urination process of a person, the sound data is analyzed by using a urine flow rate prediction model and a urination/non-urination classification model classifying urination sections and non-urination sections, so as to obtain urination data, whereby the urination information is obtained by using the obtained urination data.

Hereinafter, with reference to FIG. 1, a general environment in which the method of obtaining the above-described urination information is performed will be described.

FIG. 1 is a view illustrating an environment for analyzing urination information according to an exemplary embodiment of the present specification. Referring to FIG. 1, a sound analysis system 1000, a recording device 2000, and an external server 3000 may be used to obtain the urination information for a urination process.

The sound analysis system 1000 may obtain the urination information on the basis of data about the urination process. For example, the sound analysis system 1000 may obtain sound data recorded in the urination process by the recording device 2000, and obtain the urination information by using the obtained sound data. A process in which the sound analysis system 1000 obtains the urination information from the sound data will be described in detail later.

The sound analysis system 1000 may communicate with the external server 3000. The sound analysis system 1000 may obtain the above-described sound data from the recording device 2000 or may also obtain the sound data from the external server 3000. In addition, the sound analysis system 1000 may provide the urination information obtained by analyzing the sound data to the external server 3000. In other words, the sound analysis system 1000 may obtain the urination information by analyzing the urination-related sound data received from the outside, and output or provide the urination information to the outside.

The recording device 2000 may record sound related to urination. Specifically, the recording device 2000 may be worn by a person or installed in a space where the person urinates so as to record sound generated in the urination process. For example, the recording device 2000 may include a wearable device, which is equipped with a recording function, such as a smart watch, a smart band, a smart ring, and a smart neckless, or may include a smart phone, a tablet, a desktop, a laptop, a portable recorder, an installation-type recorder, or the like.

The recording device 2000 may obtain sound data by recording sound in the urination process.

Here, the sound data may be obtained by digitizing analog acoustic signals for the urination process. For example, the recording device 2000 may include an analog to digital converter (ADC) module, and obtain the sound data from the acoustic signals for the urination process by using specific sampling rates such as 8 kHz, 16 kHz, 22 kHz, 32 kHz, 44.1 kHz, 48 kHz, 96 kHz, 192 kHz, or 384 kHz.

The recording device 2000 may provide the obtained sound data to the sound analysis system 1000 and/or the external server 3000. To this end, the recording device 2000 may perform wired and/or wireless data communication with the sound analysis system 1000 and/or the external server 3000.

The recording device 2000 may also be used as a means for transmitting urination information to a user. For example, the recording device 2000 may obtain the urination information from the sound analysis system 1000 and output the urination information to the user.

The external server 3000 may store or provide various data. For example, the external server 3000 may store sound data obtained from the recording device 2000 or urination information obtained from the sound analysis system 1000. As another example, the external server 3000 may provide sound data obtained from the recording device 2000 to the sound analysis system 1000, and provide urination information obtained from the sound analysis system 1000 to the recording device 2000.

Meanwhile, the sound analysis system 1000 and the recording device 2000 may be implemented as one device. For example, the sound analysis system 1000 may obtain sound data by including a module having a recording function thereof. As another example, components of the sound analysis system 1000 may be built in the recording device 2000, providing a function by which the recording device 2000 analyzes sound data independently.

Sound Analysis System

Hereinafter, the configuration and operation process of the sound analysis system 1000 will be described in detail with reference to FIGS. 2 and 3.

Figure 2:
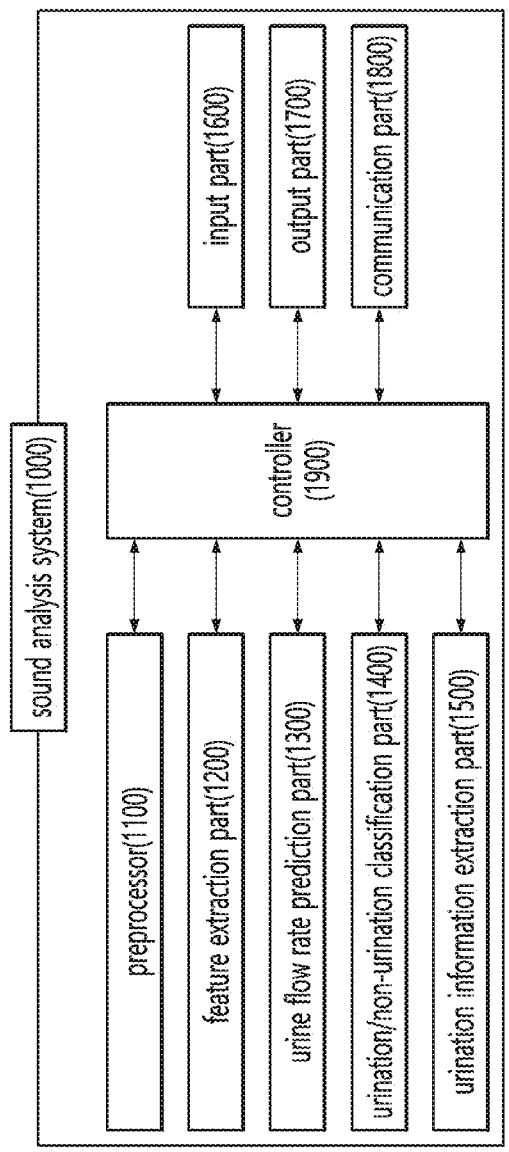
FIG. 2 is a view illustrating a configuration of a sound analysis system according to the exemplary embodiment of the present specification.

FIG. 2 is a view illustrating a configuration of a sound analysis system according to the exemplary embodiment of the present specification.

Figure 3:
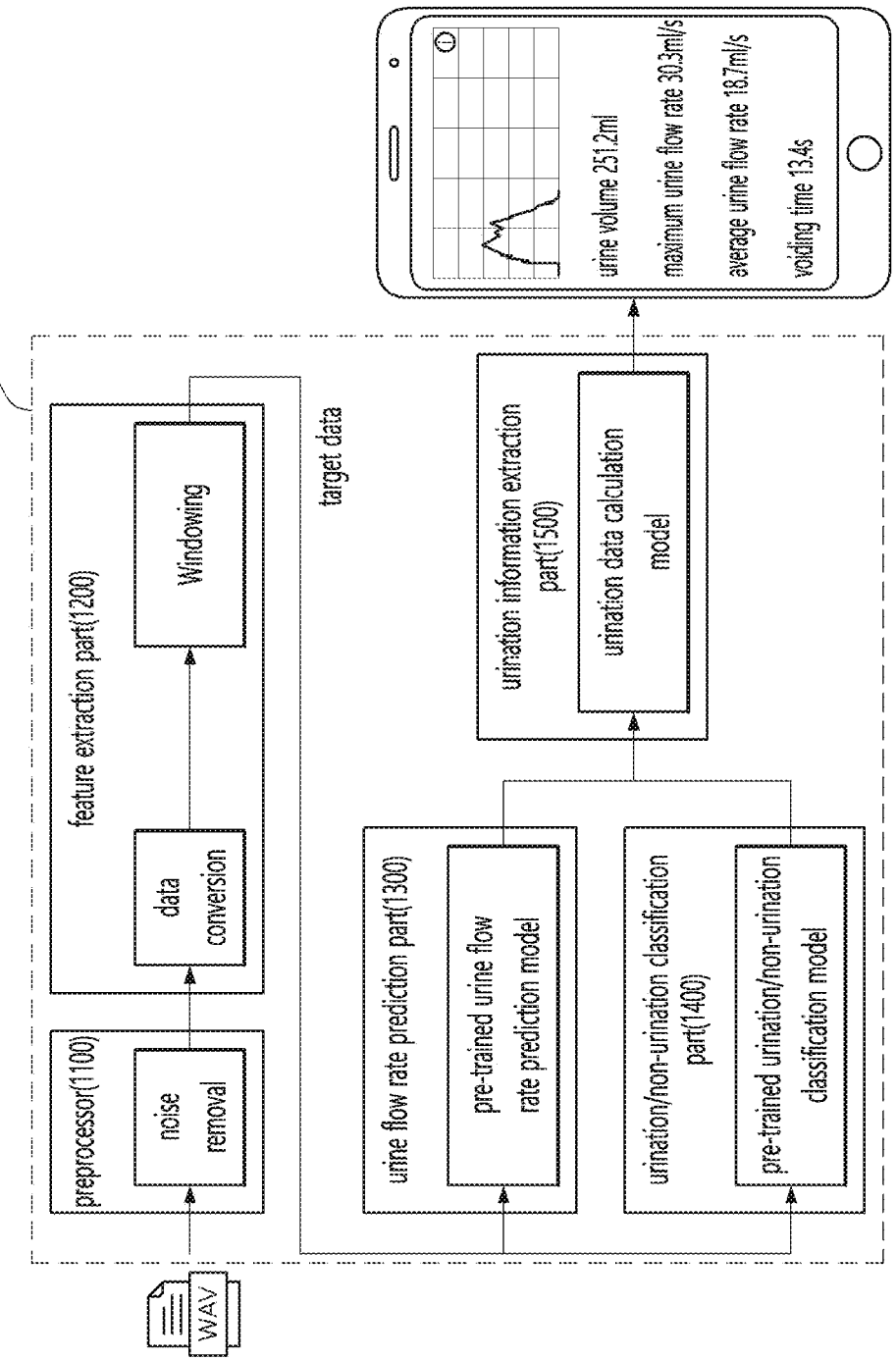
FIG. 3 is a view illustrating a process by which the configuration of the sound analysis system works according to the exemplary embodiment of the present specification.

FIG. 3 is a view illustrating a process by which the configuration of the sound analysis system works according to the exemplary embodiment of the present specification.

Referring to FIG. 2, the sound analysis system 1000 may include: a preprocessor 1100, a feature extraction part 1200, a urine flow rate prediction part 1300, a urination/non-urination classification part 1400, a urination information extraction part 1500, an input part 1600, an output part 1700, a communication part 1800, and a controller 1900.

The preprocessor 1100 may perform pre-processing on sound data received by the sound analysis system 1000. The pre-processing is a process performed prior to extracting feature values from the sound data, and may include filtering as described below.

In the preprocessor 1100, filtering for noise removal may be performed on the sound data. Here, the filtering may refer to a process of excluding noise-related data from the sound data, and to this end, a high-pass filter, a low-pass filter, a band-pass filter, and the like may be used. The filtering of the preprocessor 1100 may be omitted.

Meanwhile, in the preprocessor 1100, windowing, which will be described later, may be performed.

The feature extraction part 1200 may extract feature values from the pre-processed sound data. Here, the feature values may refer to numerical values obtained by quantifying unique features of the sound data. For example, the feature values may include at least one of a time domain spectrum magnitude value, a value of spectral centroid, a frequency domain spectrum magnitude value, a frequency domain root mean square (RMS) value, a spectrogram magnitude value, a Mel-spectrogram magnitude value, a bispectrum score (BGS), a non-Gaussianity score (NGS), formants frequencies (FF), a value of Log Energy (Log E), a zero crossing rate (ZCR), a value of kurtosis (Kurt), and a Mel-Frequency cepstral coefficient (MFCC). The feature extraction part 1200 may convert the preprocessed sound data and extract feature values therefrom. The feature extraction part 1200 may change a conversion form depending on feature values to be extracted from the sound data. For example, when the feature values to be extracted are spectrum values, the feature extraction part 1200 may convert the preprocessed sound data into spectrum data having a frequency axis. As another example, when the feature values to be extracted are Mel-spectrogram image values, the feature extraction part 1200 may convert the preprocessed sound data into spectrogram image data having a time axis and a frequency axis. When there is provided a plurality of types of feature values to be extracted, the feature extraction part 1200 may convert the preprocessed sound data into various types of data. Hereinafter, for convenience of description, a case where the feature values to be extracted by the feature extraction part 1200 are values of a Mel-spectrogram image will be mainly described, but the technical idea of the present specification is not limited thereto, and may be similarly applied to a case where the feature values have different forms.

The feature extraction part 1200 may obtain segmented target data through windowing for Mel-spectrogram image data obtained by converting the pre-processed sound data. Here, the windowing may refer to dividing sound data or converted data between a starting point and an ending point thereof by using each window having a time interval of a predetermined size. A specific windowing method will be described later.

The segmented target data obtained through windowing may be understood as vector data, matrix data, or data having other formats in each window section. For example, the segmented target data may be understood as a set of vector data in which values of the above-described Mel-spectrogram image are arranged in a row in each window section. As another example, the segmented target data may be understood as a set of data in a matrix form for the values of the above-described Mel-spectrogram image in consideration of a time axis and a frequency axis in each window section.

Meanwhile, the feature extraction part 1200 may divide the sound data into different segmented sound data through windowing prior to converting the sound data to extract the feature values. Alternatively, the windowing is performed in the preprocessor 1100, and the feature extraction part 1200 may be configured to obtain segmented sound data from the preprocessor 1100, to extract feature values by converting the obtained segmented sound data into data (e.g., a spectrum, a spectrogram, or a Mel-spectrogram, and the like) including the feature values, and to obtain data in a vector form, a matrix form, or other forms of the extracted feature values as segmented target data.

The feature extraction part 1200 may transmit the segmented target data to the urine flow rate prediction part 1300 and/or the urination/non-urination classification part 1400.

The urine flow rate prediction part 1300 may predict a urine flow rate during urination. For example, the urine flow rate prediction part 1300 may calculate predicted urine flow rate values for the sound data by using a pre-trained urine flow rate prediction model.

The urine flow rate prediction model may refer to a model trained by using machine learning. Here, the machine learning may be understood as a comprehensive concept including an artificial neural network and further including deep-learning. For example, the urine flow rate prediction model may be implemented by an artificial neural network trained with a training data set in which the data obtained by precisely measuring urine flow rates in the urination process is labeled on the sound data obtained by recording sound in the corresponding urination process. The structure and training method of the urine flow rate prediction model will be described in detail later.

The urine flow rate prediction part 1300 may obtain urine flow rate values over time in the urination process by using the urine flow rate prediction model and provide the urine flow rate values to the urination information extraction part 1500.

The urination/non-urination classification part 1400 may classify urination sections and non-urination sections in the urination process. For example, the urination/non-urination classification part 1400 may obtain classification data, which classifies the urination sections and the non-urination sections, from the sound data by using a pre-trained urination/non-urination classification model.

The urination/non-urination classification model may refer to a model trained by using machine learning. For example, the urination/non-urination classification model may be implemented by an artificial neural network trained with a training data set in which the data indicating the urination/non-urination sections obtained by using urine volume data precisely measured in the urination process is labeled on the sound data obtained by recording sound in the corresponding urination process. The structure and training method of the urination/non-urination classification model will be described in detail later.

The urination/non-urination classification part 1400 may obtain classification values, which indicate whether urination or non-urination, over time in the urination process by using the urination/non-urination classification model, and provide the classification values to the urination information extraction part 1500.

The urination information extraction part 1500 may obtain urination information for the urination process. For example, the urination information extraction part 1500 may generate urination data by using the urine flow rate values obtained from the above-described urine flow rate prediction part 1300 and the classification values obtained from the urination/non-urination classification part 1400, and may extract the urination information from the generated urination data.

Specifically, the urination information extraction part 1500 may generate candidate urine flow rate data for the sound-recorded urination process by using the obtained urine flow rate values. In addition, the urination information extraction part 1500 may generate urination classification data for the sound-recorded urination process by using the obtained classification values. The urination information extraction part 1500 may obtain urination data based on the candidate urine flow rate data and the urination classification data, which are described above, by using a urination data calculation model. Here, the urination data may be understood as a set of urine flow rate values over time for the sound-recorded urination process.

The urination information extraction part 1500 may extract the urination information from the urination data. Here, the urination information in the urination process may include: a maximum flow rate, an average flow rate, a urine volume, a starting time point and an ending time point of urination, a urine flow time, a time to maximum urine flow rate, a voiding time (with or without interruption time), and the like.

The preprocessor 1100, the feature extraction part 1200, the urine flow rate prediction part 1300, the urination/non-urination classification part 1400, and the urination information extraction part 1500, which are described above, may refer to software programs. For example, processes of noise removal and windowing of the preprocessor 1100, processes of data conversion and a target data generation of the feature extraction part 1200, the urine flow rate prediction model of the urine flow rate prediction part 1300, the urination/non-urination classification model of the urination/ non-urination classification part 1400, and the urination data calculation model of the urination information extraction part 1500 may be stored in a memory part (not shown) of the sound analysis system 1000 to be described later in a form of a plurality of functions or instructions, and may be loaded and performed by the controller 1900.

The input part 1600 may receive a user input from a user. The user input may be conducted in various forms including a key input, a touch input, and a voice sound input. The input part 1600 is a comprehensive concept that includes, for example, not only a traditional keypad, a keyboard, and a mouse, but also a touch sensor for sensing a user's touch and various other types of input means for detecting or receiving various types of user inputs.

The output part 1700 may output urination information and provide the urination information to a user. The output part 1700 is a comprehensive concept that includes a display for outputting images, a speaker for outputting sound, a haptic device for generating vibration, and various other types of output means.

The communication part 1800 may communicate with an external device. The sound analysis system 1000 may transmit/receive data to and from the recording device 2000 or the external server 3000 through the communication part 1800. For example, the sound analysis system 1000 may provide urination information to the recording device 2000 and/or the external server 3000 through the communication part 1800, and receive sound data from the recording device 2000 and/or the external server 3000.

The controller 1900 may control the overall operation of the sound analysis system 1000. For example, the controller 1900 may obtain urination information from sound data by loading and executing programs related to the preprocessor 1100, the feature extraction part 1200, the urine flow rate prediction part 1300, the urination/non-urination classification part 1400, and the urination information extraction part 1500. The controller 1900 may be implemented as a central processing unit (CPU) or a device similar to the central processing unit according to hardware, software, or a combination thereof. In hardware, the controller may be provided in a form of an electronic circuit that performs a control function by processing electrical signals, and in software, the controller may be provided in a form of a program or codes for driving a hardware circuit.

The sound analysis system 1000 may further include a memory part for storing various types of information. Various data may be temporarily or semi-permanently stored in the memory part. Examples of the memory part may include a hard disk (HDD), a solid state drive (SSD), a flash memory, a read-only memory (ROM), a random access memory (RAM), etc. The memory part may be provided in a form embedded in the sound analysis system 1000 or in a detachable form.

Sound Analysis Process

Hereinafter, each step of the sound analysis process performed in the above-described sound analysis system 1000 will be described in detail with reference to FIGS. 4 to 14.

Window Division Method

Figure 4:
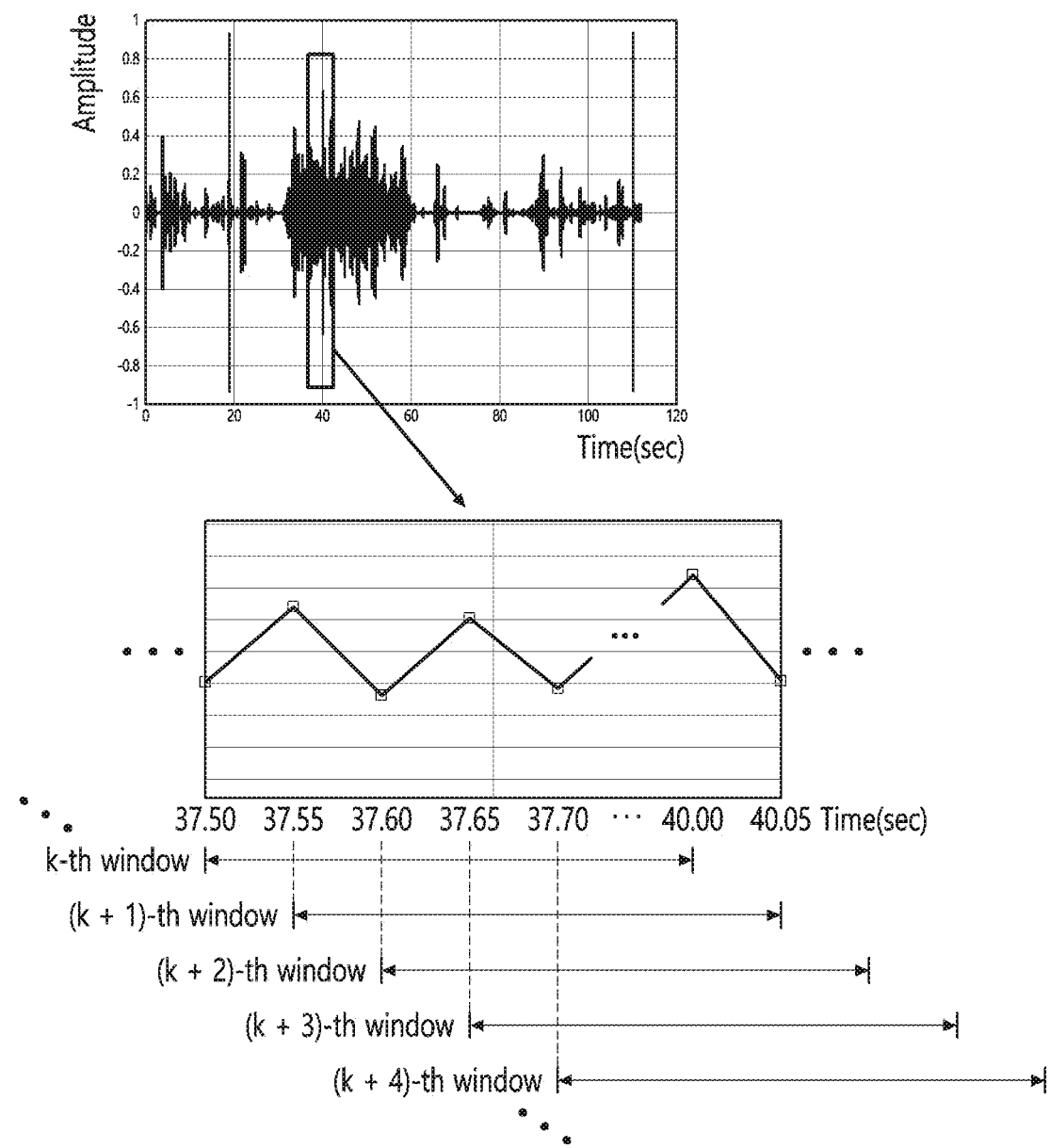
FIGS. 4 and 5 are views illustrating a method of dividing sound data according to windows according to the exemplary embodiment of the present specification.
Figure 5:
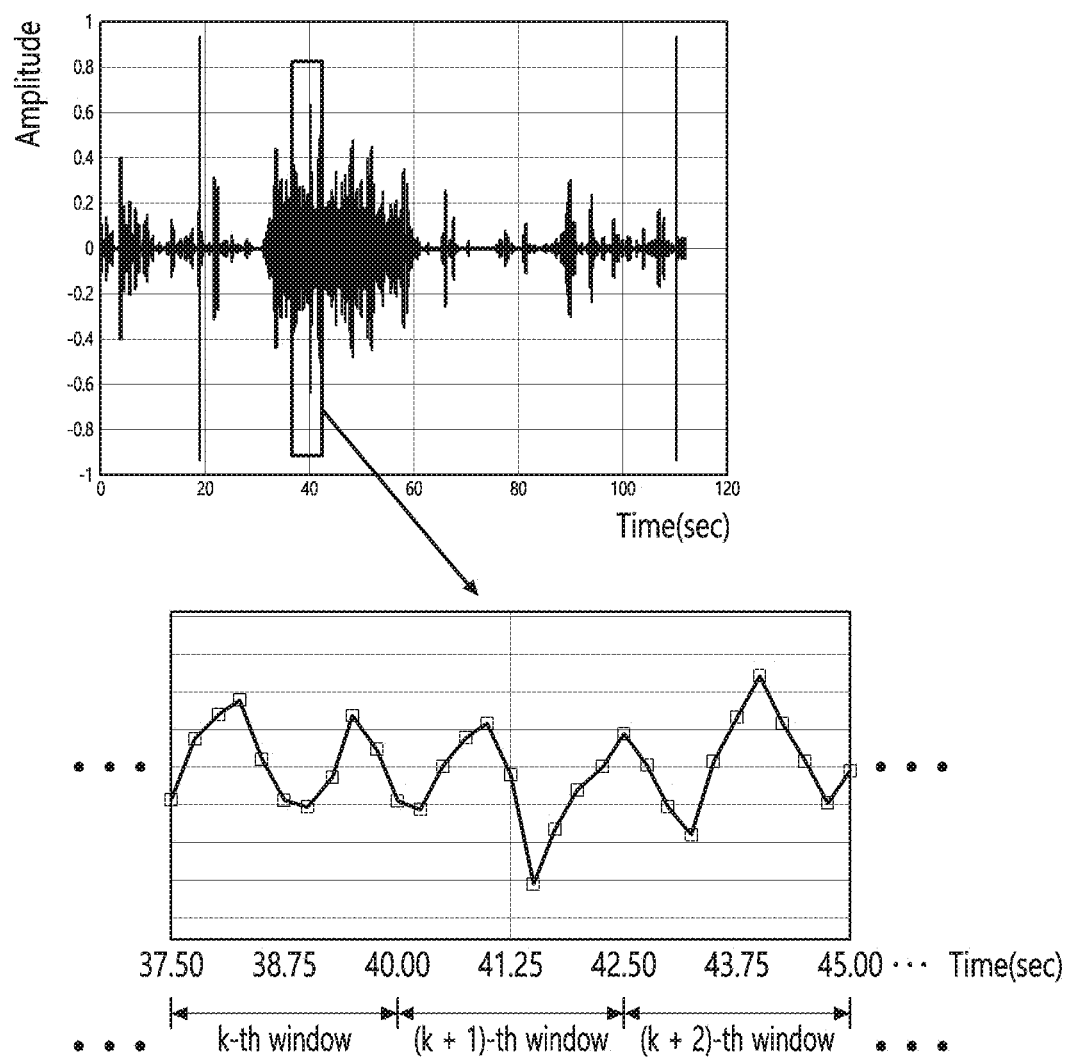

FIGS. 4 and 5 are views illustrating a method of dividing sound data according to windows according to the exemplary embodiment of the present specification. Hereinafter, a method of dividing windows for sound data will be described for convenience of description, but the method of dividing windows may be equally applied not only to the sound data but also to data obtained by converting the sound data in order to extract feature values.

The sound data may have a starting point and an ending point. In this case, a length of the sound data may be determined as a time interval between the starting point and the ending point. The length of the sound data may be determined according to a length of the recorded sound data.

The sound data may be divided into at least one or more of windows. For example, the sound data may be divided into at least one or more windows sequentially determined between the starting point and the ending point, and then segmented sound data corresponding to each window may be obtained. Here, the sequential determination of at least one or more windows means that a plurality of windows is sequentially arranged from the starting point to the ending point of the sound data. Meanwhile, at least one or more windows may be assigned to a specific section between the starting point and the ending point of the sound data in time series. Each window may have a predetermined size. The size of a window may be determined according to the length of the sound data and the number of windows to divide the sound data. In addition, when the number of windows is plural, the consecutive windows may overlap each other.

For example, referring to FIG. 4, sound data having 0 seconds as a starting point, and 120 seconds as an ending point may be divided into the plurality of windows having a size of 2.5 seconds. Specifically, considering a time interval from 37.5 seconds to 40.05 seconds, which is a part of the sound data, a k-th window may correspond to a time interval from 37.50 seconds to 40.00 seconds, a (k+1)-th window may correspond to a time interval from 37.55 seconds to 40.05 seconds, a (k+2)-th window may correspond to a time interval from 37.60 to 40.10 seconds, a (k+3)-th window may correspond to a time interval from 37.65 seconds to 40.15 seconds, and a (k+4)-th window may correspond a time interval from to 37.70 seconds to 40.20 seconds. As such, consecutive windows may overlap each other, and an overlapping degree may be determined according to resolution of sound data, a sliding degree of the consecutive windows, a window size, and the number of windows. For example, in FIG. 4, in the sound data, the resolution may be 0.05 seconds, the sliding degree may be 0.05 seconds, the window size may be 2.5 seconds, and the overlapping degree of the consecutive windows may be 2.45 seconds. Meanwhile, the resolution, the sliding degree, and the window size of the sound data are not limited to the above-mentioned numerical values, and may be determined such that the resolution is between about 0.01 seconds and about 2.00 seconds, the sliding degree is between about 0.01 seconds and about 5.00 seconds, and the window size is between about 0.05 and about 5.00 seconds. More preferably, the resolution may be determined between about 0.05 seconds and about 1.00 seconds, the sliding degree may be determined between about 0.05 seconds and about 2.50 seconds, and the window size may be determined between about 0.10 seconds and about 3.00 seconds.

Considering a data merging process to be described later, data accuracy may increase as the overlapping degree of consecutive windows increases, but data processing speed may be slow due to an increase in a data processing amount. Accordingly, it is necessary to determine the overlapping degree of consecutive windows in consideration of a priority between the data accuracy and the data processing speed.

As another example, referring to FIG. 5, sound data having 0 seconds as a starting point, and 120 seconds as an ending point is divided into a plurality of windows having a size of 2.5 seconds, but unlike FIG. 4, consecutive windows may not overlap each other. Specifically, referring to a time interval of 37.5 seconds to 45 seconds, the time interval being a part of sound data, the k-th window may correspond to a time interval from 37.50 seconds to 40.00 seconds, the (k+1)-th window may correspond to a time interval from 40.00 seconds to 42.50 seconds, and the (k+2)-th window may correspond to a time interval from 42.50 seconds to 45.00 seconds. When sound data is divided into windows so that consecutive windows do not overlap, data accuracy may be lowered in the data merging process to be described later, but data processing speed may be relatively fast because the data processing amount is reduced.

In dividing the sound data into the plurality of windows, whether the consecutive windows overlap or not and the overlapping degree at a time when the windows overlap may vary depending on target data to be obtained from the sound data.

As an example, in predicting a urine flow rate in the urination process by using sound data, the sound data is divided into the plurality of windows in that high accuracy is required for predicted urine flow rate values, but as shown in FIG. 4, it may be preferable to improve the accuracy by overlapping the consecutive windows.

As another example, in classifying the urination process into urination sections and non-urination sections by using sound data, the sound data is divided into a plurality of windows in that the determination of whether urination or non-urination is relatively easy and thus accuracy is generally high, but it may be preferably that a sliding degree of each window is increased to be lower than an overlapping degree of consecutive windows in the process of predicting the above-described urine flow rate, or the consecutive windows are not allowed to overlap as shown in FIG. 5, so as to improve the data processing speed.

Hereinafter, a case for convenience of description is mainly described, wherein in the process of predicting a urine flow rate, sound data is divided into the plurality of windows so that consecutive windows overlap, and in the process of classifying the urination sections and the non-urination sections, the sound data is divided into the plurality of windows so that the overlapping degree of the consecutive windows is lower than that of the process of predicting the urine flow rate or the consecutive windows do not overlap, but the technical idea of the present specification is not limited thereto. It is natural that in both of the process of predicting the urine flow rate and the process of classifying the urination sections and the non-urination sections, the sound data may be divided into the plurality of windows so that the overlapping degree of the consecutive windows is the same, or conversely, in both of the processes, the sound data may be divided into the plurality of windows so that the consecutive windows do not overlap.

Feature Value Extraction

Figure 6:
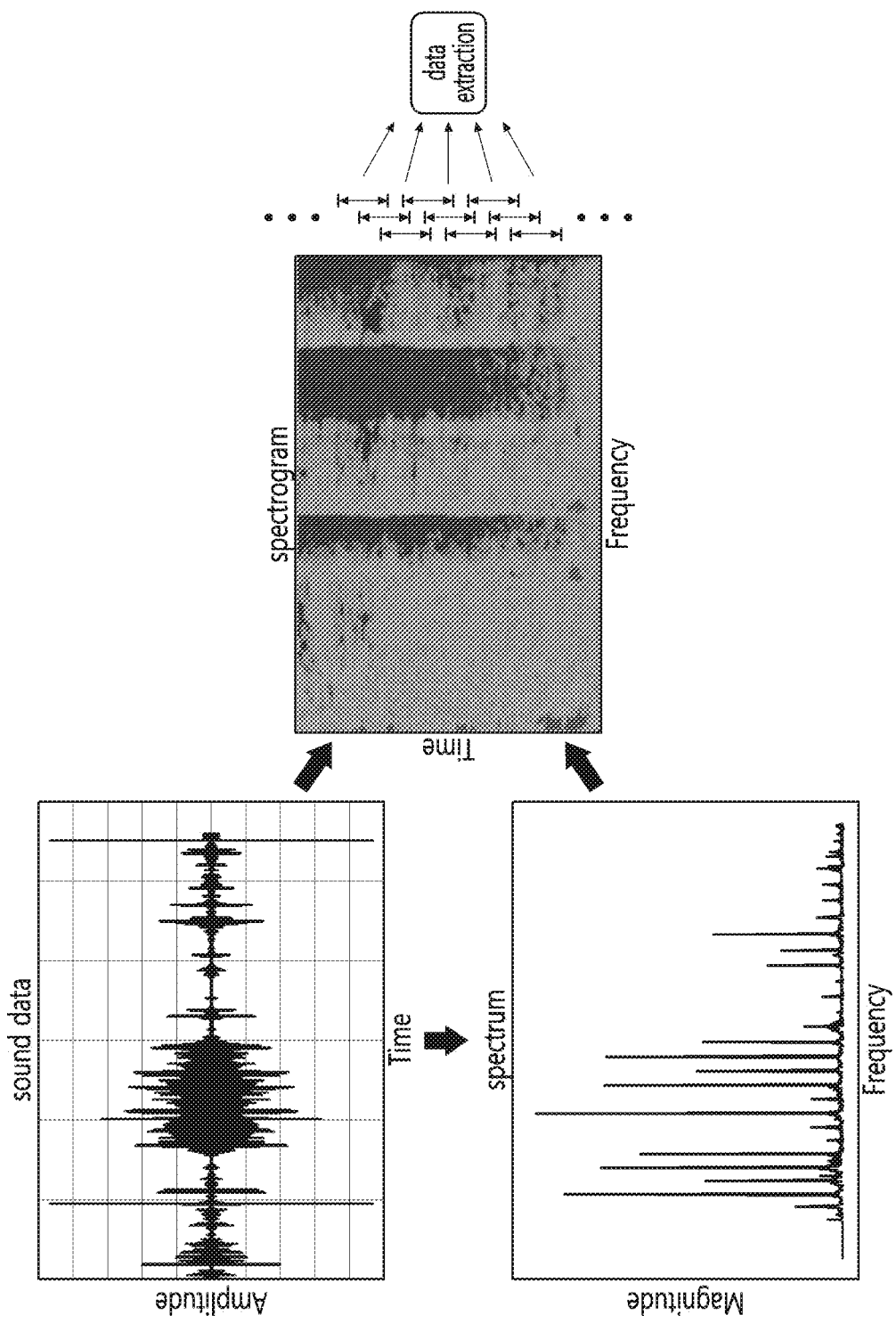
FIG. 6 is a view illustrating a process of extracting feature values from the sound data according to the exemplary embodiment of the present specification.

FIG. 6 is a view illustrating a process of extracting feature values from the sound data according to the exemplary embodiment of the present specification. Here, the feature values are mainly described as being extracted from an image data of a spectrogram, but naturally, the case of extracting other types of feature values described above may also be included in the technical idea of the present specification.

Sound data may generally include amplitude values over time. The sound data may be converted, through processing, into spectrum data including magnitude values depending on frequencies. Here, the spectrum data may be obtained by using Fourier transform (FT), Fast Fourier transform (FFT), Discrete Fourier transform (DFT), and Short-time Fourier transform (STFT).

A spectrogram image may be obtained by using the above-described sound data and spectrum data. Here, the spectrogram image may be a Mel-spectrogram image to which a Mel-scale is applied.

The feature extraction part 1200 may extract data from the spectrogram image. Data extraction may be understood as a process in which spectrogram image values respectively corresponding to the plurality of windows dividing sound data are extracted.

Obtainment of Target Data for Analysis

Figure 7:
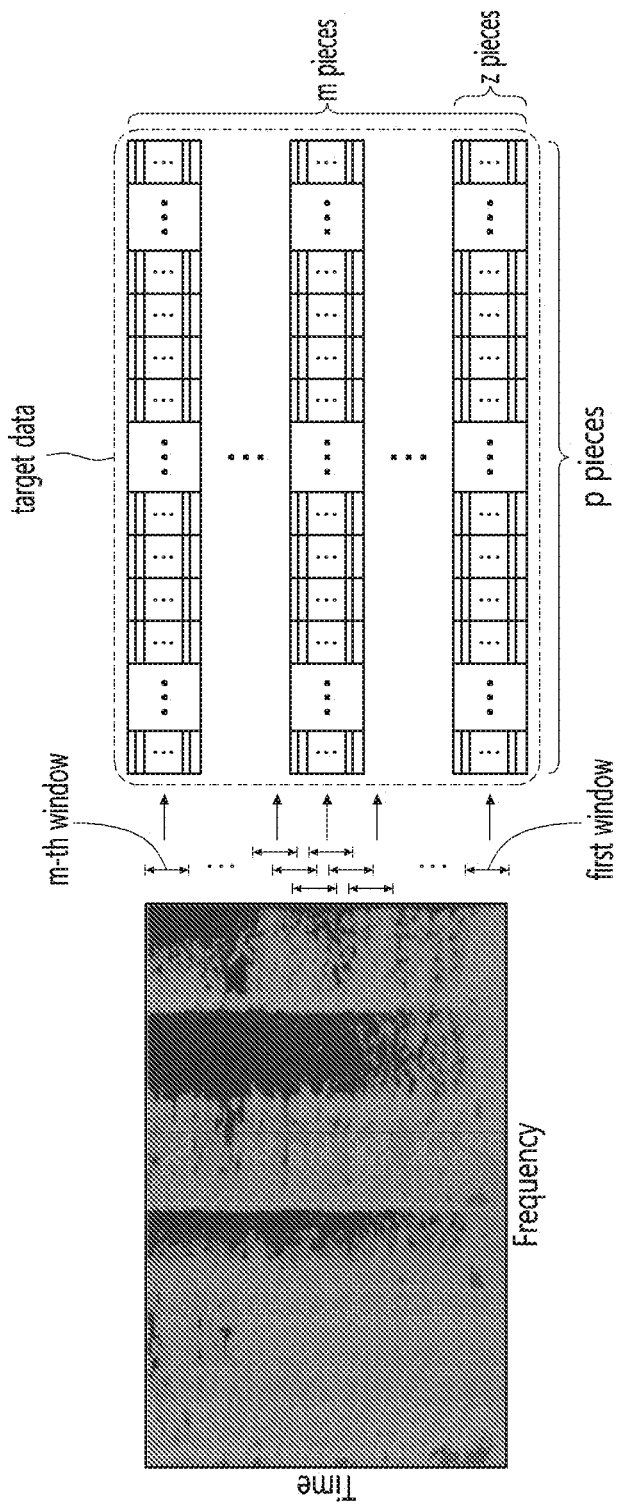
FIGS. 7 and 8 are views illustrating a process of obtaining target data to be analyzed according to the exemplary embodiment of the present specification.
Figure 8:
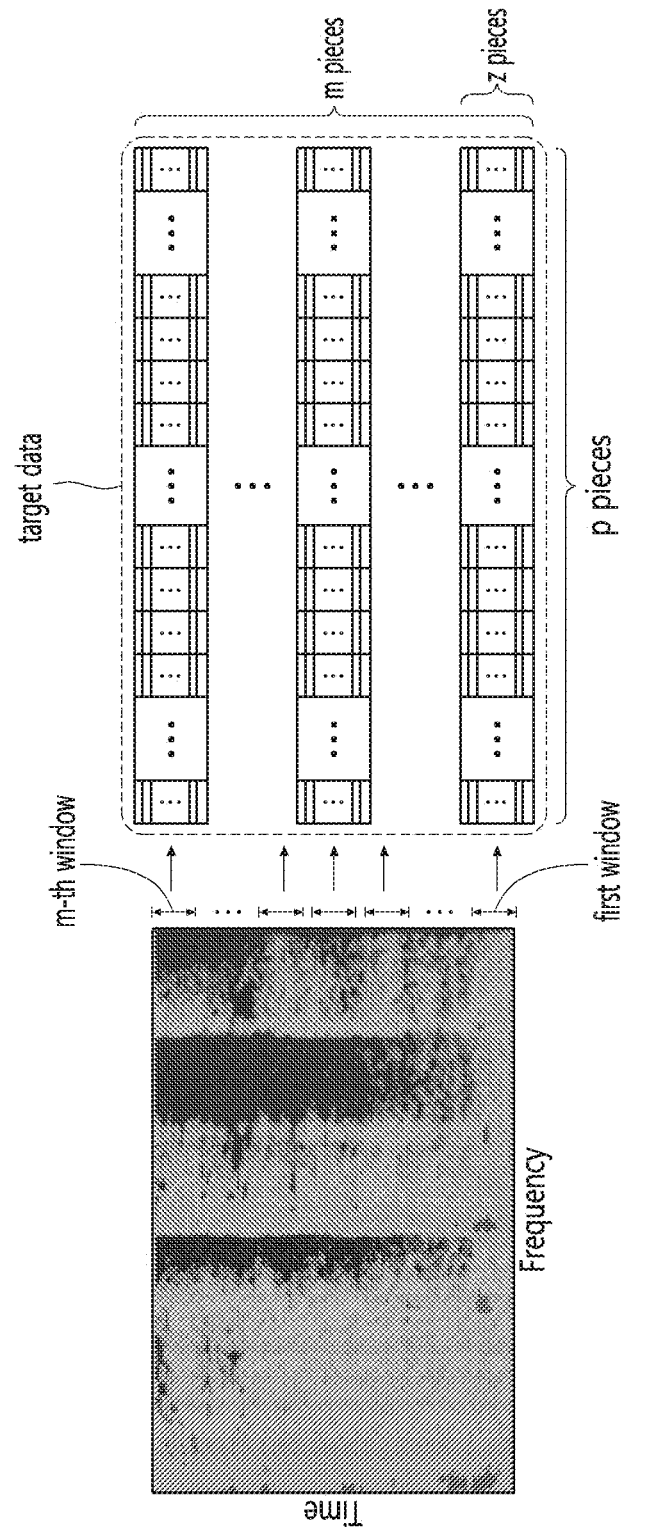

FIGS. 7 and 8 are views illustrating a process of obtaining target data to be analyzed according to the exemplary embodiment of the present specification.

The target data may refer to a set of data generated by extracting feature values from the converted sound data. For example, a plurality of segmented target data may be generated from a spectrogram image of the sound data, and target data may be understood as a set of the plurality of segmented target data.

The number of target data, that is, the number of segmented target data included in the target data may be the same as the number of windows. For example, referring to FIG. 7, when the sound data is divided into first to m-th windows (where, m is a natural number greater than or equal to 2), the target data may include first to m-th segmented target data respectively corresponding to the first to m-th windows. As another example, when the sound data is divided into first to n-th windows (where, n is a natural number greater than or equal to 2), the target data may include first to n-th segmented target data respectively corresponding to the first to n-th windows.

Meanwhile, the number of segmented target data included in the target data may not be equal to the number of windows. For example, the target data may include the number of segmented target data greater than the number of windows.

The size of each segmented target data may be determined according to a unit time (or resolution) of a time axis of a spectrogram, the number of unit sections on a frequency axis, and a window size. For example, assuming that a size of one segmented target data is $z*p$, where the unit time of the time axis of the spectrogram is 0.05 seconds, the number of unit sections on the frequency axis is 512, and the window size is 2.5 seconds, it may be that $z=2.5/0.05=50$, and $p=512$.

As a method of dividing sound data into a plurality of windows in the process of generating target data, a method of dividing consecutive windows so as to overlap as shown in FIG. 7, and a method of dividing consecutive windows so as not to overlap as shown in FIG. 8 may be used.

The number of target data used in the urine flow rate prediction model or the number of target data used in the urination/non-urination classification model, which are to be described later, may be different from each other. For example, the number of target data used in the urine flow rate prediction model may be greater than the number of target data used in the urination/non-urination classification model.

In this case, the target data used for the urine flow rate prediction model and the target data used for the urination/non-urination classification model may be generated from the spectrogram image, separately. Here, the size of each segmented target data included in the target data used in the urine flow rate prediction model and the size of each segmented target data included in the target data used in the urination/non-urination classification model are the same, but the total number of segmented target data used in each model may be different.

Alternatively, at least some of the target data generated from the spectrogram image may be used for the urine flow rate prediction model, and at least some of the target data generated from the spectrogram image may be used for the urination/non-urination classification model. For example, the entire first to m-th segmented target data generated from the spectrogram image may be used for the urine flow rate prediction model, and the first to n-th segmented target data of the first to m-th segmented target data (where, n is greater than or equal to 2 and less than m) may be used for the urination/non-urination classification model. Here, the first to m-th segmented target data may respectively correspond to the first to m-th windows in which the sound data or spectrogram image data is divided so that consecutive windows overlap. The first to n-th segmented target data may respectively correspond to n data of which the windows among the first to m-th windows have an overlapping degree smaller than an overlapping degree of consecutive windows of the urine flow rate prediction model or do not overlap each other.

As described above, by varying the number of segmented target data used in the urine flow rate prediction model and the urination/non-urination classification model, the accuracy may be increased in the urine flow rate prediction model and the data processing speed may be increased in the urination/non-urination classification model.

Meanwhile, the number of segmented target data used in the urine flow rate prediction model or the urination/non-urination classification model may be the same. For example, the first to m-th segmented target data generated from the spectrogram image may be input to each of the urine flow rate prediction model and the urination/non-urination classification model.

In addition, it is natural that a form (e.g., a data size, a total number, and the like) of the segmented target data used in the urine flow rate prediction model and a form of the segmented target data used in the urination/non-urination classification model may be different depending on the training method.

Urine Flow Rate Prediction Method

Hereinafter, a process of obtaining candidate urine flow rate data from target data will be described with reference to FIGS. 9 and 10.

Figure 9:
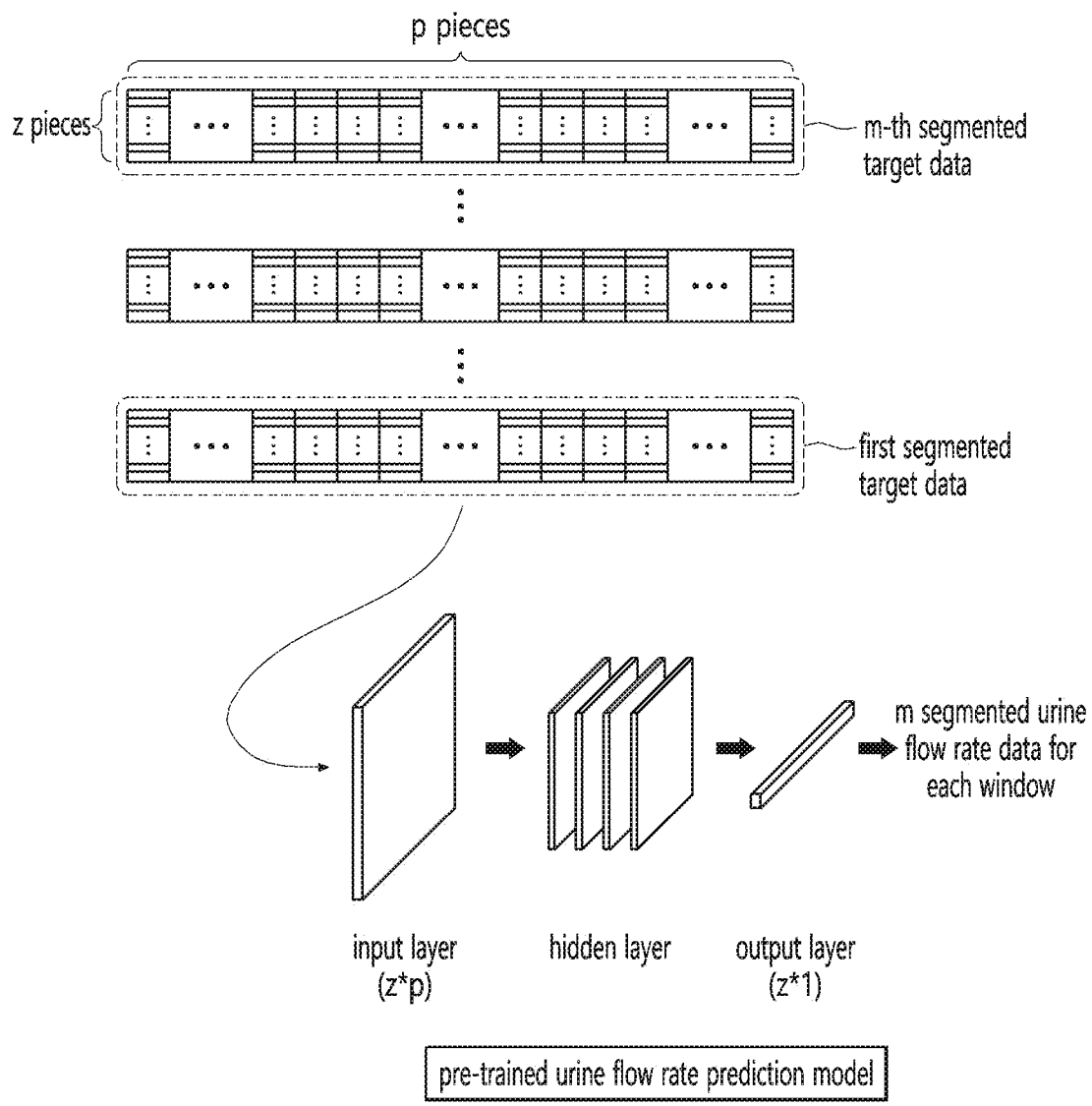
FIG. 9 is a view illustrating a process of obtaining urine flow rate data by using a urine flow rate prediction model according to the exemplary embodiment of the present specification.

FIG. 9 is a view illustrating a process of obtaining urine flow rate data by using a urine flow rate prediction model according to the exemplary embodiment of the present specification.

Referring to FIG. 9, the urine flow rate prediction model may receive inputs of first to m-th segmented target data, and obtain first to m-th segmented urine flow rate data.

The urine flow rate prediction model is a model trained by using machine learning, and may use, as the algorithm thereof, at least any one of k-nearest neighbors, linear regression, logistic regression, a support vector machine (SVM), a decision tree, a random forest, or a neural network. Here, at least one of an artificial neural network (ANN), a time delay neural network (TDNN), a deep neural network (DNN), a convolution neural network (CNN), a recurrent neural network (RNN), or a long short-term memory (LSTM) may be selected as the neural network therefrom.

As an example, referring to FIG. 9, the urine flow rate prediction model may include an input layer, a hidden layer, and an output layer.

Here, the input layer may have an input size of $z*p$ and sequentially receive first to m-th segmented target data.

Alternatively, the input layer may have an input size of m*z*p and receive first to m-th segmented target data at once.

Here, when the urine flow rate prediction model uses the CNN algorithm, the hidden layer may include a convolution layer, a pooling layer, and a fully-connected layer.

Here, the output layer may output segmented urine flow rate data including urine flow rate values. In this case, the segmented urine flow rate data output from the output layer may correspond to windows corresponding to the input target data. For example, when first segmented target data corresponding to a first window is input to the urine flow rate prediction model and first segmented urine flow rate data is output, the first segmented urine flow rate data may include urine flow rate values corresponding to the first window. Specifically, the first segmented urine flow rate data may include predicted urine flow rate values per unit time interval in the first window, that is, for a time interval equal to a window size from a starting point of the sound data, and the number of the predicted urine flow rate value may be determined according to the size of the aforementioned target data, or according to a unit time of a time axis of a spectrogram (e.g., when the unit time of the time axis of the spectrogram is 0.05 seconds and the window size is 2.5 seconds, the number of predicted urine flow rate values included in one segmented urine flow rate data is 2.5/0.05=50).

Meanwhile, the urine flow rate prediction model performs a function of outputting the predicted urine flow rate values, and unlike the urination/non-urination classification model to be described later, the urine flow rate prediction model does not use an activation function or classifier, such as a step function, a sigmoid function, or a Softmax function.

Figure 10:
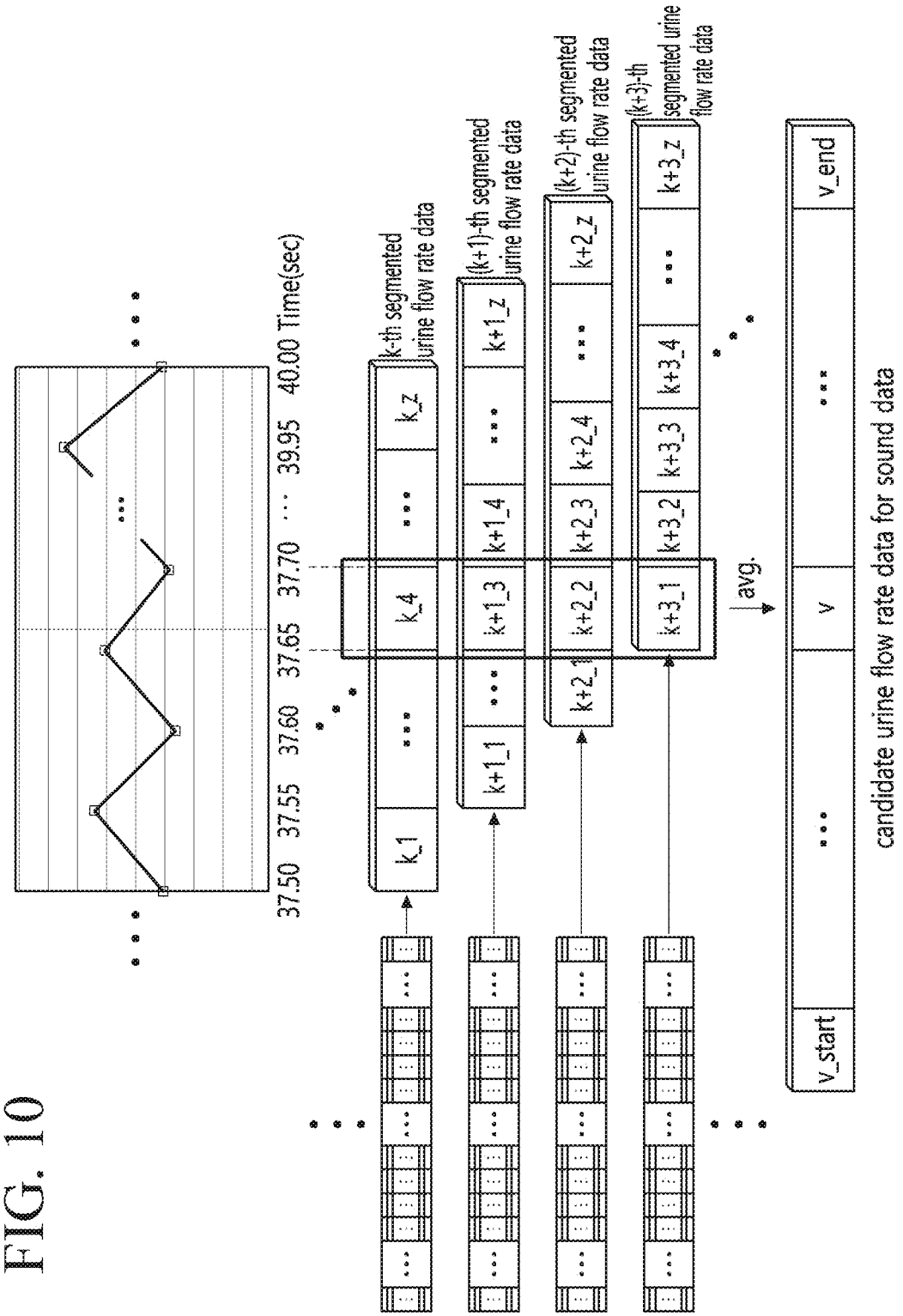
FIG. 10 is a view illustrating a method of obtaining candidate urine flow rate data according to the exemplary embodiment of the present specification.

FIG. 10 is a view illustrating a method of obtaining candidate urine flow rate data according to the exemplary embodiment of the present specification.

The urination information extraction part 1500 may generate candidate urine flow rate data by processing segmented urine flow rate data. Here, the candidate urine flow rate data may include predicted urine flow rate values over time in the sound-recorded urination process. Each predicted urine flow rate value included in the candidate urine flow rate data may be obtained from a plurality of segmented urine flow rate data. Specifically, the predicted urine flow rate values of a specific time interval in the candidate urine flow rate data may be obtained by using the predicted urine flow rate values (e.g., by using an average value or a median value) corresponding to the specific time interval in each of the entire segmented urine flow rate data.

As an example, referring to FIGS. 4 and 10, when some of data output through the urine flow rate prediction model is called k-th to (k+3)-th segmented urine flow rate data, and when k-th segmented urine flow rate data corresponds to the k-th window of 37.50 seconds to 40.00 seconds, (k+1)-th segmented urine flow rate data corresponds to the (k+1)-th window of 37.55 seconds to 40.05 seconds, (k+2)-th segmented urine flow rate data corresponds to the (k+2)-th window of 37.60 seconds to 40.10 seconds, and (k+3)-th segmented urine flow rate data corresponds to the (k+3)-th window of 37.65 seconds to 40.15 seconds, a predicted urine flow rate value corresponding to 37.65 seconds to 37.70 seconds among candidate urine flow rate data for sound data may be calculated by an average value obtained by using a predicted urine flow rate value (k, 4) corresponding to 37.65 seconds to 37.70 seconds in the k-th segmented urine flow rate data, a predicted urine flow rate value (k+1, 3) corresponding to 37.65 seconds to 37.70 seconds in the (k+1)-th segmented urine flow rate data, a predicted urine flow rate value (k+2, 2) corresponding to 37.65 seconds to 37.70 seconds in the (k+2)-th segmented urine flow rate data, a predicted urine flow rate value (k+3, 1) corresponding to 37.65 seconds to 37.70 seconds in the (k+3)-th segmented urine flow rate data, and predicted a urine flow rate value corresponding to 37.65 seconds to 37.70 seconds in each of the segmented urine flow rate data before the k-th segmented urine flow rate data.

In the above description, the case where the target data used in the urine flow rate prediction model is obtained on the basis of the sound data divided into the plurality of windows overlapping with each other has been described, but the target data used in the urine flow rate prediction model may also be obtained on the basis of the sound data divided by the plurality of windows not overlapping with each other. In this case, the candidate urine flow rate data may be obtained by concatenating the segmented urine flow rate data that do not overlap each other in the time domain through an operation of data concatenation, which will be described later.

Meanwhile, the candidate urine flow rate data may be generated by a method different from the above-described method. For example, the candidate urine flow rate data may be generated by using spectrum data obtained by converting the sound data. Specifically, to this end, segmented spectrum data corresponding to each time window is obtained by dividing the sound data into a plurality of non-overlapping time windows, a frequency domain of the segmented spectrum data is divided into a plurality of frequency windows, RMS values in each frequency window are extracted as feature values, urine flow rate prediction values in the corresponding time window are obtained by using the feature values in each frequency window, and thus the urine flow rate prediction values respectively obtained from the plurality of time windows may be obtained as the candidate urine flow rate data.

Urination/Non-Urination Classification Method

Figure 11:
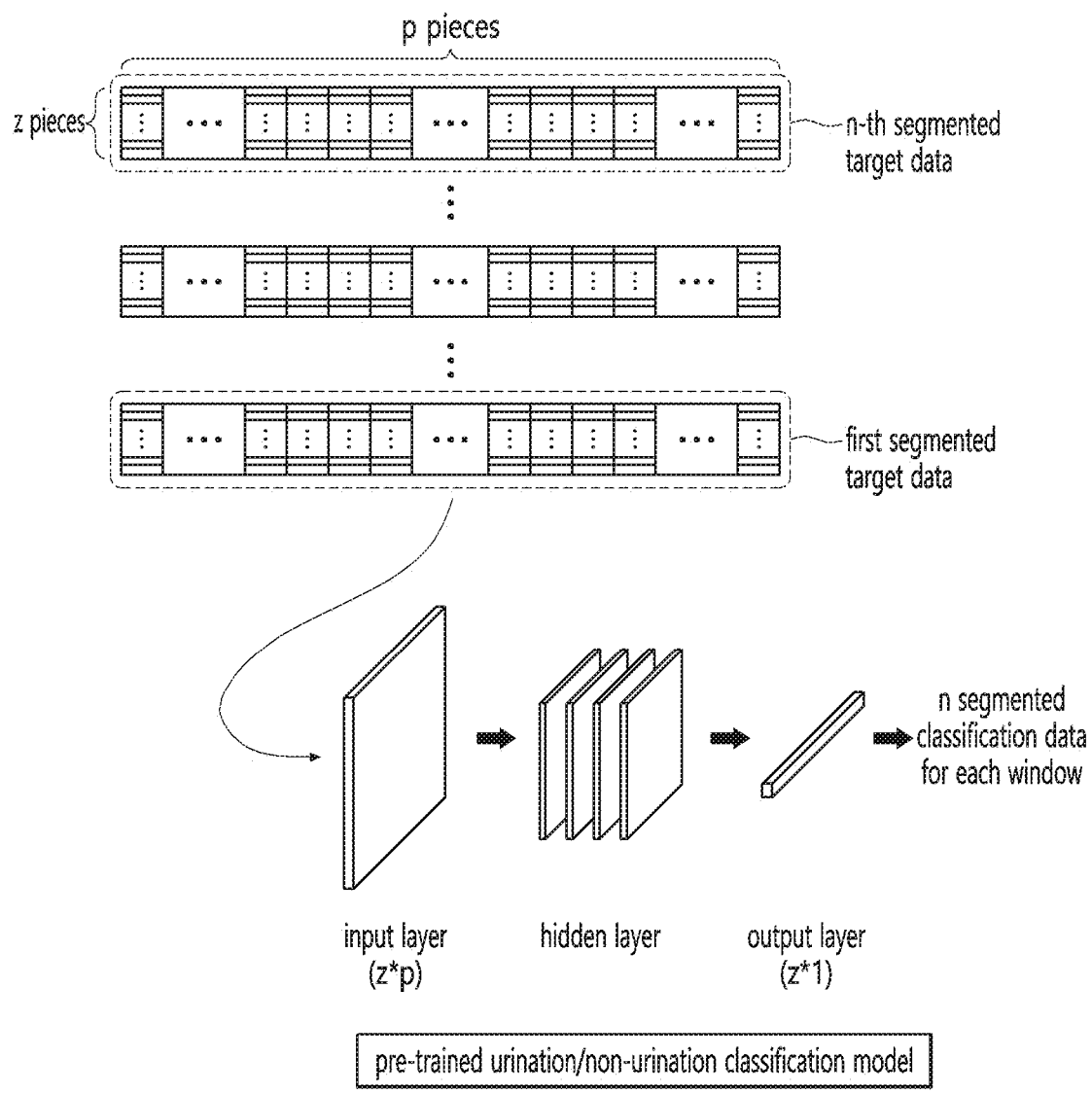
FIG. 11 is a view illustrating a process of obtaining classification data by using a urination/non-urination classification model according to the exemplary embodiment of the present specification.

FIG. 11 is a view illustrating a process of obtaining classification data by using a urination/non-urination classification model according to the exemplary embodiment of the present specification.

Referring to FIG. 11, the urination/non-urination classification model may obtain first to n-th segmented classification data by receiving first to n-th segmented target data.

The urination/non-urination classification model is a model trained by using machine learning, and at least any one of k-nearest neighbors, linear regression, logistic regression, a support vector machine, a decision tree, a random forest, or a neural network may be used as the algorithm. Here, at least one of ANN, TDNN, DNN, CNN, RNN, or LSTM may be selected as the neural network. The urination/non-urination classification model may have the same structure as the above-described urine flow rate prediction model.

As an example, referring to FIG. 11, the urination/non-urination classification model may include an input layer, a hidden layer, and an output layer.

Here, the input layer may have an input size of z*p and receive first to n-th segmented target data, sequentially. Alternatively, the input layer may have an input size of n*z*p and receive first to n-th segmented target data at once.

Here, when the urination/non-urination classification model uses the CNN algorithm, the hidden layer may include a convolution layer, a pooling layer, and a fully-connected layer.

Here, the output layer may output segmented classification data including classification values. In this case, the segmented classification data output from the output layer may correspond to windows corresponding to the input segmented target data. For example, when first segmented target data corresponding to a first window is input to the urination/non-urination classification model to output first segmented classification data, the first segmented classification data may include predicted classification values corresponding to the first window. Specifically, the first segmented classification data may include the predicted classification values per unit time interval in the first window, i.e., for a time interval having a length equal to the window size from a starting point of the sound data, and the number of the predicted classification values may be determined according to the size of the aforementioned segmented target data or the unit time of the time axis of the spectrogram (e.g., when the unit time of the time axis of the spectrogram is 0.05 seconds and the window size is 2.5 seconds, the number of predicted classification values included in one segmented classification data is 2.5/0.05=50).

The predicted classification values output through the urination/non-urination classification model may be values representing the probability of being a urination section or a non-urination section. For example, it may be understood that the predicted classification values have a value between 0 and 1, and the closer to 1, the higher the probability of being the urination section, and the closer to 0, the higher the probability of being the non-urination section. In this case, the urination information extraction part 1500 described later may use the activation function or the classifier such as the step function, the sigmoid function, or the Sofiniax function, so as to change the predicted classification values or a value generated by using the predicted classification values to a value indicating the urination section or a value indicating the non-urination section.

Meanwhile, the predicted classification values output through the urination/non-urination classification model may be either a value indicating a urination section (e.g., 1) or a value indicating a non-urination section (e.g., 0). In order to provide predicted classification values in a form of a value indicating a specific class as described above, the urination/non-urination classification model may use the Softmax function or the Sofiniax classifier, unlike the aforementioned urine flow rate prediction model.

Figure 12:
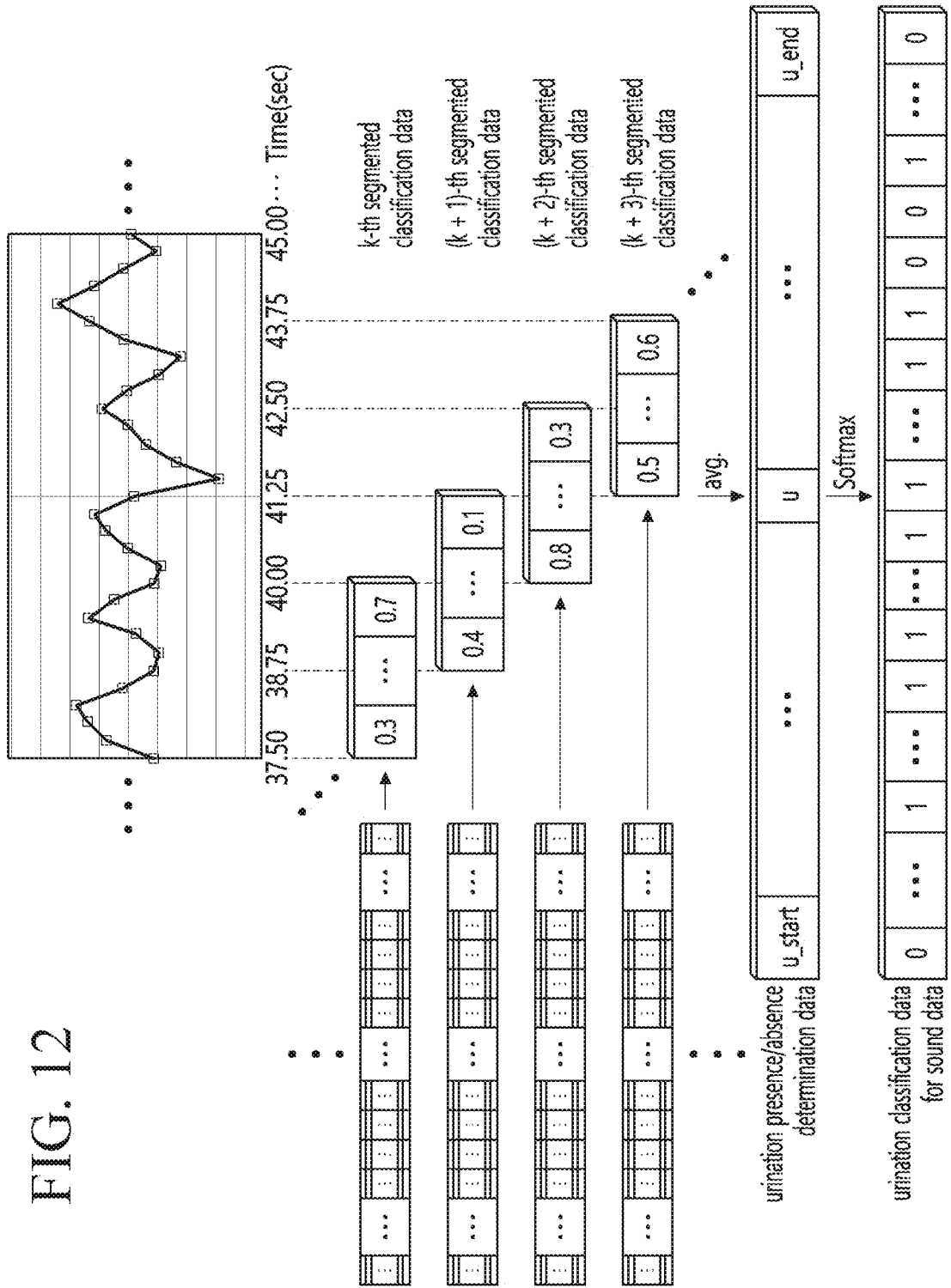
FIG. 12 is a view illustrating a method of obtaining urination classification data according to the exemplary embodiment of the present specification.

FIG. 12 is a view illustrating a method of obtaining urination classification data according to the exemplary embodiment of the present specification.

The urination information extraction part 1500 may generate urination classification data by processing a plurality of segmented classification data.

First, the urination information extraction part 1500 may generate urination present/absence determination data by processing the plurality of segmented classification data. The urination presence/absence determination data may include values related to whether urination or non-urination over time in the sound-recorded urination process. Here, the values, related to whether urination or non-urination, included in the urination presence/absence determination data may be understood as a probability value of being a urination section or a probability value of being a non-urination section. Each of the values included in the urination presence/absence determination data may be obtained from the plurality of segmented classification data. Specifically, the value corresponding to a specific window (or a specific time interval) in the urination presence/absence determination data may be obtained by using predicted classification values (e.g., by using an average value or a median value) corresponding to the specific window (or the specific time interval) in each of the entire segmented classification data.

As an example, referring to FIG. 12, when the size of a window that divides sound data is 2.5 seconds and a sliding degree is 1.25 seconds, k-th to (k+3)-th segmented classification data, which are some of the data output through the urination/non-urination classification model, may respectively correspond to a time interval from 37.50 seconds to 40.00 seconds, a time interval from 38.75 seconds to 41.25 seconds, a time interval from 40.00 seconds to 42.50 seconds, and a time interval from 41.25 seconds to 43.75 seconds. A value in a specific window of the urination presence/absence determination data may be obtained by an average value or a median value of predicted classification values corresponding to the specific window in each of the segmented classification data.

The urination present/absence determination data may be used to determine the presence or absence of a urination section, which will be described later.

The urination information extraction part 1500 may obtain urination classification data for sound data by processing urination presence/absence determination data. For example, the urination information extraction part 1500 may apply the step function, the sigmoid function, the Sofiniax function, or the like to the urination presence/absence determination data, so as to generate urination classification data that includes a value (e.g., 1) indicating a urination section or a value (e.g., 0) indicating a non-urination section.

Figure 13:
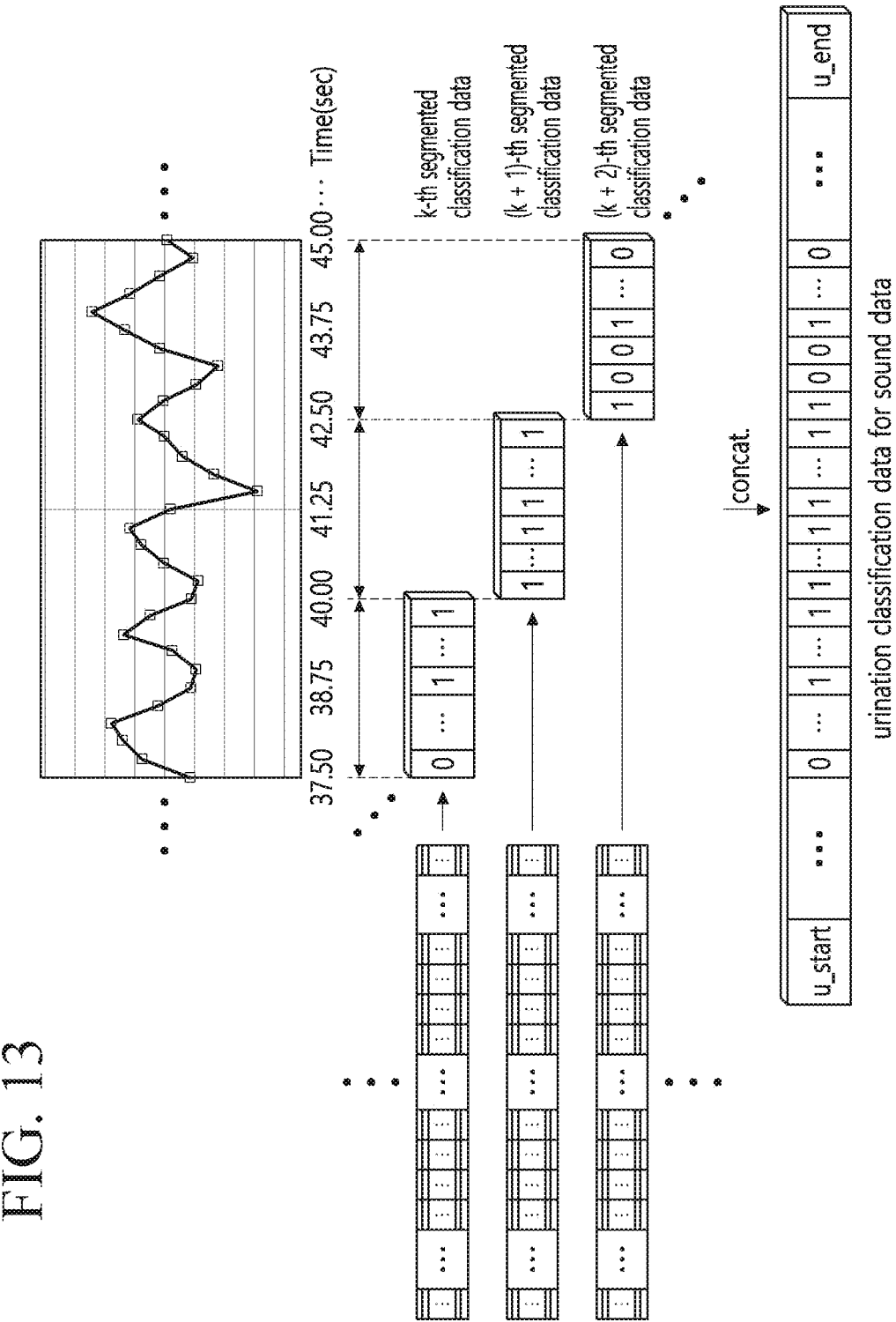
FIG. 13 is a view illustrating a method of obtaining urination classification data according to another exemplary embodiment of the present specification.

FIG. 13 is a view illustrating a method of obtaining urination classification data according to another exemplary embodiment of the present specification.

The urination information extraction part 1500 may generate urination classification data by processing the segmented classification data. Here, the urination classification data may include predicted classification values over time in the sound-recorded urination process. Each of the predicted classification values included in the urination classification data may be obtained by concatenating the plurality of segmented classification data. Specifically, predicted classification values of a specific time interval in the urination classification data may be obtained as predicted classification values corresponding to the specific time interval in segmented classification data corresponding to a window including the specific time interval. Here, each predicted classification value may be a probability value related to a urination section or a non-urination section (e.g., it may be understood as a value between 0 and 1, and the closer to 1, the higher a probability of being a urination section). Alternatively, a predicted classification value may be a value indicating a urination section (e.g., 1) or a value indicating a non-urination section (e.g., 0).

As an example, referring to FIGS. 5 and 13, when some of the data output through the urination/non-urination classification model is called k-th to (k+2)-th segmented classification data, and when a k-th segmented classification data corresponds to a k-th window of 37.50 seconds to 40.00 seconds, a (k+1)-th segmented classification data corresponds to a (k+1)-th window of 40.00 seconds to 42.50 seconds, and a (k+2)-th segmented classification data corresponds to a (k+2)-th window of 42.50 seconds to 45.00 seconds, the predicted classification values of urination classification data for sound data may be obtained such that predicted classification values corresponding to 37.50 seconds to 40.00 seconds are predicted classification values (0, . . . , 1, . . . , 1) of the k-th segmented classification data, predicted classification values corresponding to 40.00 seconds to 42.50 seconds are predicted classification values (1, . . . , 1, 1 . . . 1) of the (k+1)-th segmented classification data, and predicted classification values corresponding to 42.50 seconds to 45.00 seconds are predicted classification values (1, 0, 0, 1, . . . , 0) of the (k+2)-th segmented classification data.

Meanwhile, urination classification data may be generated by a method other than the above-described method.

For example, urination classification data may be generated by using spectrum data obtained by converting sound data. Specifically, the segmented spectrum data corresponding to respective time window is obtained by dividing the sound data into a plurality of time windows, the frequency domain of the segmented spectrum data is divided into a plurality of frequency windows, RMS values in each frequency window are extracted as feature values, whether the corresponding time window is the urination section or the non-urination interval is determined by using the feature values in each frequency window, and thus the result may be obtained as the urination classification data.

As another example, urination classification data may be generated by using sound data. Specifically, zero-crossing rates are extracted as feature values for the sound data, and urination sections and non-urination sections are determined in the sound data on the basis of the extracted feature values, and thus the result may be obtained as the urination classification data.

Urination Data Obtainment Method

Hereinafter, a method of generating urination data will be described with reference to FIGS. 14 and 15.

Figure 14:
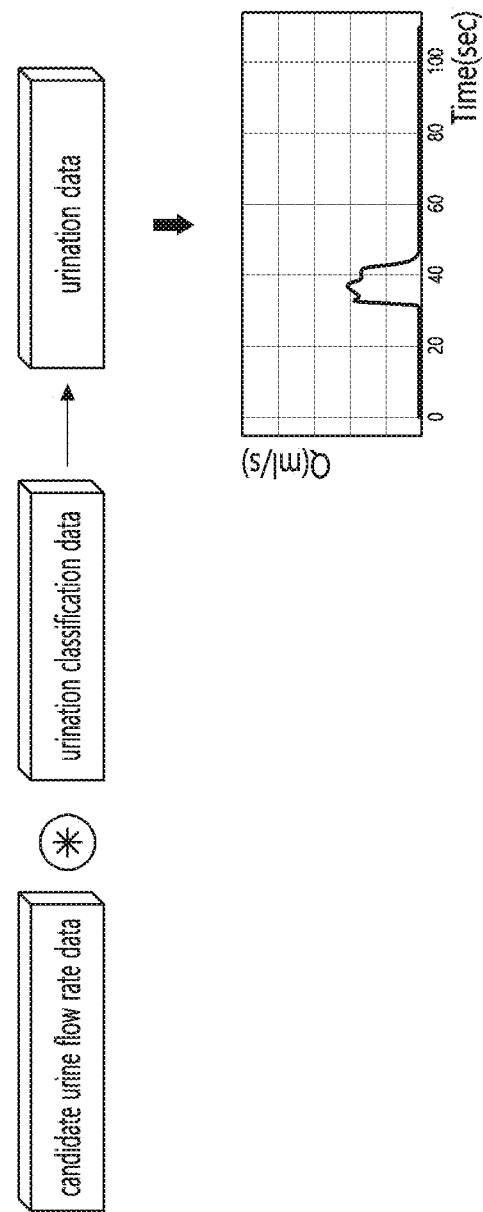
FIGS. 14 and 15 are views illustrating a method of obtaining urination data by using the candidate urine flow rate data and the urination classification data according to the exemplary embodiment of the present specification.
Figure 15:
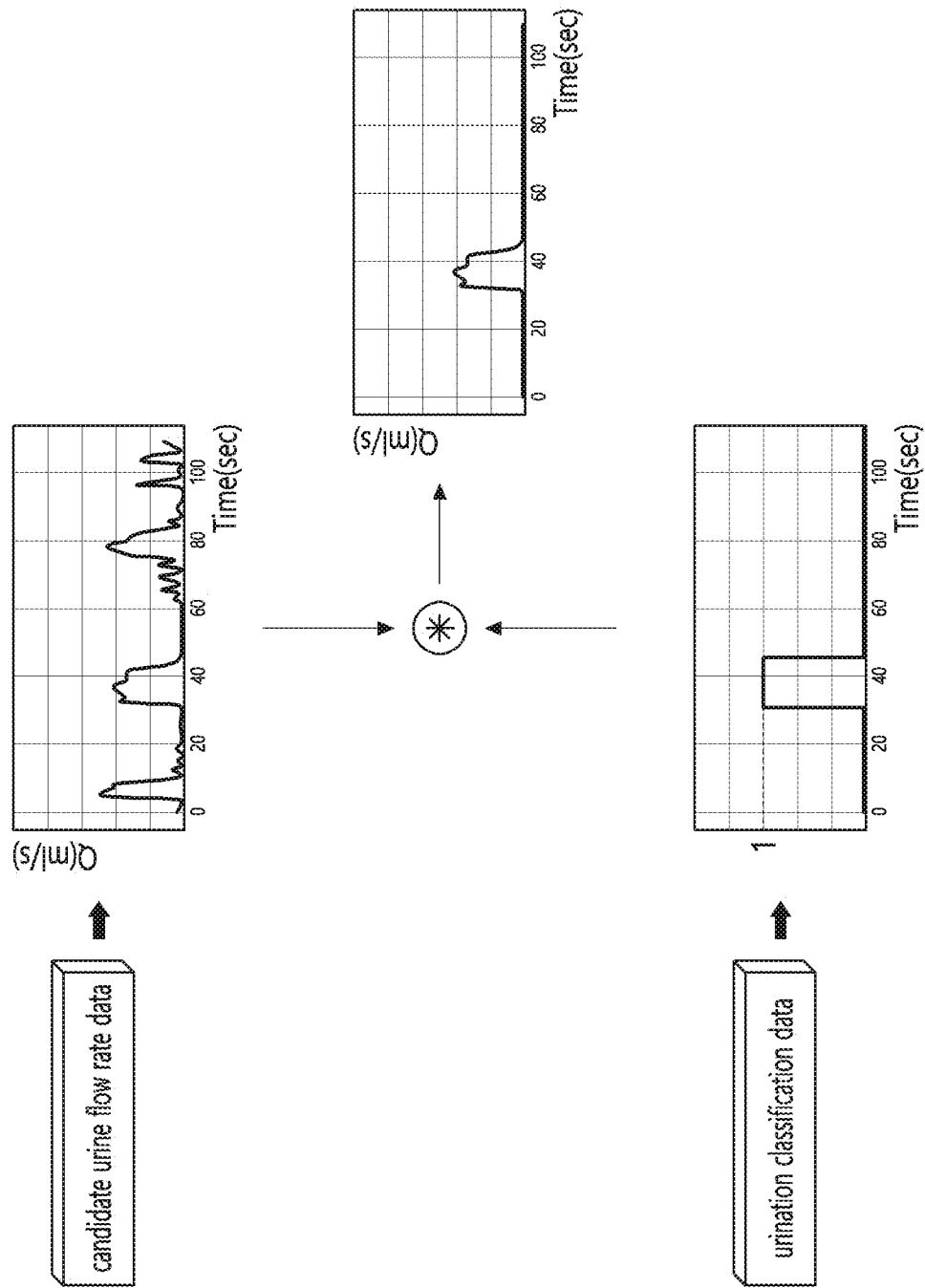

FIGS. 14 and 15 are views illustrating a method of obtaining the urination data by using the candidate urine flow rate data and the urination classification data according to the exemplary embodiment of the present specification.

The urination information extraction part 1500 may calculate urination data by using candidate urine flow rate data and urination classification data. The urination data may be obtained in a form including urine flow rate prediction values over time for a sound-recorded urination process. For example, referring to FIG. 14, the urination data may be obtained by performing convolution on the candidate urine flow rate data and the urination classification data. For another example, urination data may be obtained by multiplying each of the urine flow rate prediction values over time included in candidate urine flow rate data by each of classification prediction values over time included in urination classification data. In this case, the urination data may be expressed as a matrix of discrete values.

The urination information extraction part 1500 may extract urination information by using the obtained urination data. For example, the urination information extraction part 1500 may obtain the largest value among the predicted urine flow rate values included in the obtained urination data as the maximum urine flow rate value, and calculate a urine volume for each section or a total urine volume through discrete integration. Meanwhile, referring to FIG. 14, the urination information extraction part 1500 may obtain a urination graph for a sound-recorded urination process by processing the urination data (e.g., by smoothing, interpolation, and the like), and calculate, from the urination graph, a maximum urine flow rate value, an average urine flow rate value, a voiding time, a urine volume for each section, a total urine volume, and the like.

The urination data may be obtained by processing each of the candidate urine flow rate data and the urination classification data, and then performing calculation on the processed data. For example, referring to FIG. 15, the urination information extraction part 1500 may generate a candidate urine flow rate graph for a sound-recorded urination process by processing candidate urine flow rate data, generate a urination/non-urination section graph for the sound-recorded urination process by processing urination classification data, and obtain a urination graph for the sound-recorded urination process by performing a convolution calculation on the generated candidate urine flow rate graph and the generated urination/non-urination section graph. Here, the operation of smoothing or interpolation may be performed while processing the candidate urine flow rate data or the urination classification data.

Sound Analysis Method

Hereinafter, a method of analyzing sound to obtain urination information for a urination process by using the sound analysis system 1000 with reference to FIGS. 16 and 17 will be described in steps, but the content overlaps with the above-mentioned parts will be omitted.

Proceeding Sound Analysis without Determining Whether Urination Section Exists

Figure 16:
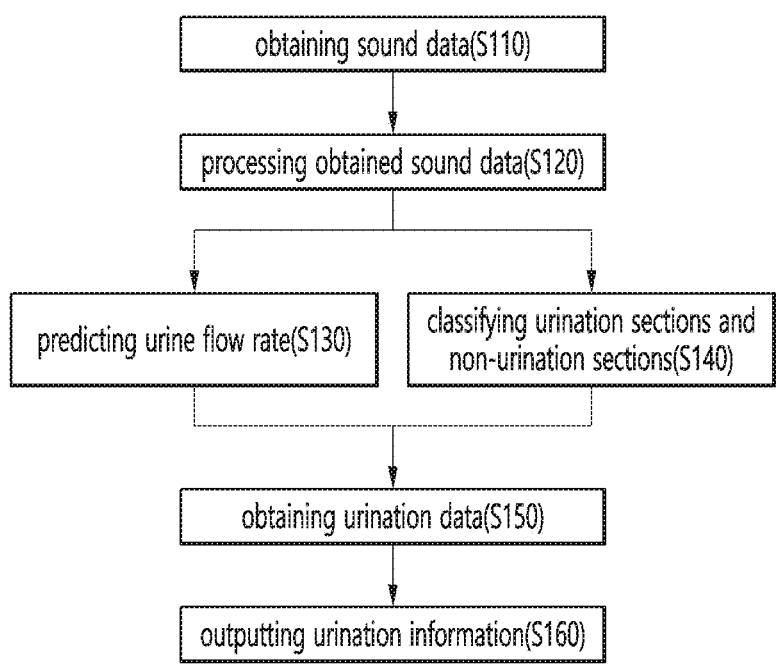
FIGS. 16 and 17 are flowcharts illustrating a method of analyzing the urination information according to the exemplary embodiment of the present specification.
Figure 17:
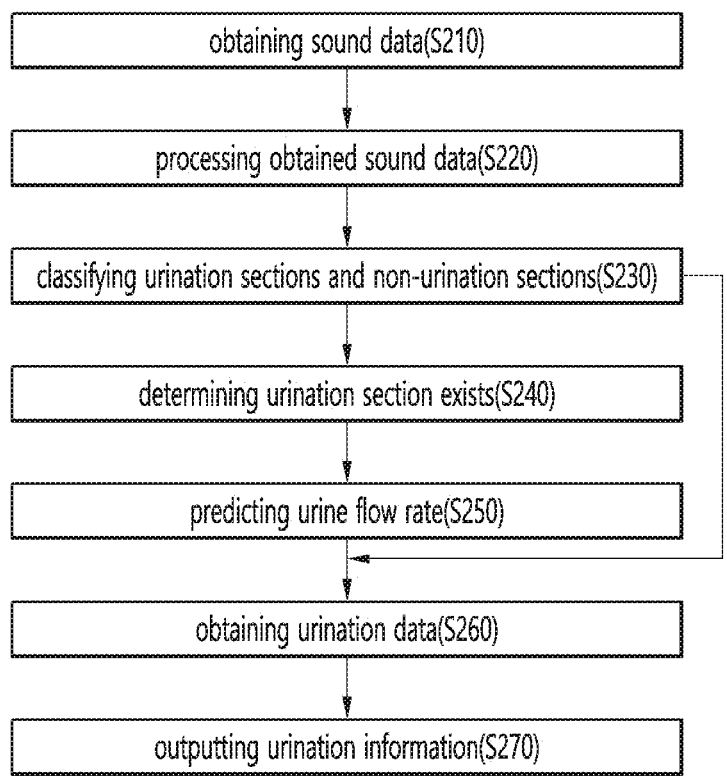

FIGS. 16 and 17 are flowcharts illustrating a method of analyzing the urination information according to the exemplary embodiment of the present specification.

Referring to FIG. 16, the method of analyzing sound may include: step S110 of obtaining sound data; step S120 of processing the obtained sound data; step S130 of predicting a urine flow rate; step S140 of classifying urination/non-urination section; step S150 of obtaining urination data; and step S160 of outputting urination information.

In step S110, a sound analysis system 1000 may obtain sound data. The sound analysis system 1000 may obtain the sound data recorded in a urination process of a person from a recording device 2000. Alternatively, the sound analysis system 1000 may obtain arbitrary sound data from outside, but the corresponding sound data may not be data recorded in the urination process.

In step S120, the sound analysis system 1000 may process the obtained sound data. The sound analysis system 1000 may process the obtained sound data by using a preprocessor 1100 and a feature extraction part 1200. Since the method of processing the sound data has been described above, a detailed description thereof will be omitted.

In step S130, the sound analysis system 1000 may predict a urine flow rate. The sound analysis system 1000 may obtain a segmented urine flow rate data group, which corresponds to each window dividing the sound data, from data obtained by processing the sound data by using the urine flow rate prediction part 1300, and may obtain candidate urine flow rate data from the segmented urine flow rate data group by using the urination information extraction part 1500. The candidate urine flow rate data may include values predicting the urine flow rate in the entire sound data. Since the process of generating the candidate urine flow rate data has been described above, specific details thereof will be omitted.

In step S140, the sound analysis system 1000 may classify urination sections and non-urination sections. The sound analysis system 1000 may obtain a segmented classification data group, which corresponds to each window dividing the sound data, from data obtained by processing the sound data by using the urination/non-urination classification part 1400, and may obtain urination classification data from the segmented classification data group by using the urination information extraction part 1500. The urination classification data may include classification values for classifying the urination sections and the non-urination sections in the overall sound data. Since the process of generating the urination classification data has been described above, specific details thereof will be omitted.

The above-described step S130 of predicting the urine flow rate and the step S140 of classifying the urination sections and the non-urination sections may be performed in parallel or sequentially.

In step S150, the sound analysis system 1000 may obtain urination data. The sound analysis system 1000 may obtain the urination data from the candidate urine flow rate data and the urination classification data by using the urination information extraction part 1500. It may be understood that the urination data includes, in the sound data, urine flow rate prediction values selected by the urination classification data from among the urine flow rate prediction values included in the candidate urine flow rate data. Since the process of generating the urination data has been described above, specific details thereof will be omitted.

In step S160, the sound analysis system 1000 may output urination information. The sound analysis system 1000 may extract the urination information from the urination data by using the urination information extraction part 1500, may provide the extracted urination information to a user through an output part 1700, or may provide to a recording device 2000 and/or an external server 3000. Here, as shown in FIG. 3, the output urination information may include a urine volume, a maximum urine flow rate, an average urine flow rate, and a voiding time.

Proceeding Sound Analysis after Determining Whether Urination Section Exists

Meanwhile, the method of analyzing urination information may perform determination of whether urination exists prior to predicting a urine flow rate in order to improve efficiency in the data processing process.

Referring to FIG. 17, the method of analyzing urination information may include: step S210 of obtaining sound data; step S220 of processing the obtained sound data; step S230 of classifying urination sections and the non-urination sections; step S240 of determining whether a urination section exists; step S250 of predicting a urine flow rate; step S260 of obtaining urination data; and step S270 of outputting urination information. Here, since step S210 of obtaining the sound data, step S220 of processing the obtained sound data, and step S270 of outputting the urination information are described above in FIG. 16, redundant content will be omitted.

In step S230, a sound analysis system 1000 may classify urination/non-urination sections prior to predicting a urine flow rate. By using the urination/non-urination classification part 1400 and the urination information extraction part 1500, the sound analysis system 1000 may obtain urination classification data from data obtained by processing the sound data.

In step S240, the sound analysis system 1000 may determine whether a urination section exists. The sound analysis system 1000 may determine whether the sound data is data obtained by recording sound in the urination process by using the urination classification data obtained in step S230 of classifying the urination/non-urination. For example, the sound analysis system 1000 may determine whether a urination section exists between a starting point and an ending point of the sound data.

As an example, the sound analysis system 1000 may determine whether the urination process is reflected in the sound data on the basis of the above-described urination presence/absence determination data. For convenience of explanation, values included in the urination presence/absence determination data are referred to as determination values. The sound analysis system 1000 may determine that the urination process is reflected in the sound data when at least one of the determination values included in the urination presence/absence determination data is greater than or equal to a threshold value. Alternatively, the sound analysis system 1000 may determine that the urination process is reflected in the sound data when a ratio of any determination value greater than or equal to the threshold value among the determination values included in the urination presence/absence determination data is greater than or equal to a predetermined ratio (e.g., 5% to 50%). The threshold value for determining whether a urination section exists may be set in various ways. For example, the threshold value may be determined as a value between 0.30 and 0.95. More preferably, the threshold value may be determined as a value between 0.50 and 0.80.

As another example, the sound analysis system 1000 may determine whether the urination process is reflected in the sound data on the basis of the urination classification data. Specifically, when the number of classification values indicating the urination sections in the urination classification data is greater than or equal to a predetermined number, the sound analysis system 1000 may determine that the sound related to the urination process is reflected in the sound data. Alternatively, the sound analysis system 1000 may calculate a ratio of the number of classification values indicating the urination sections to the number of classification values indicating the non-urination sections in the urination classification data, and when the calculated ratio is greater than or equal to the predetermined ratio, the sound analysis system 1000 may determine that the urination sections exist.

According to the above-described determination method in step S240 of determining whether a urination section exists, the sound analysis system 1000 may generate only urination presence/absence determination data, or generate both of the urination presence/absence determination data and the urination classification data.

When it is determined that a urination section exists in the sound data, the sound analysis system 1000 may enter step S260 of predicting the urine flow rate, and when it is determined that a urination section does not exist in the sound data, the sound analysis system 1000 may terminate the sound analysis. In a case of determining whether a urination section exists by using the urination presence/absence determination data, when it is determined that a urination section does not exist in the sound data, the sound analysis system 1000 may not generate urination classification data from the urination presence/absence determination data.

In step S250, when it is determined that a urination section exists in the sound data, the sound analysis system 1000 may predict a urine flow rate. The sound analysis system 1000 may obtain a segmented urine flow rate data group, which corresponds to each window dividing the sound data, from data obtained by processing the sound data by using the urine flow rate prediction part 1300, and may obtain candidate urine flow rate data from the segmented urine flow rate data group by using the urination information extraction part 1500. The candidate urine flow rate data may include values predicting urine flow rates from the overall sound data. Since the process of generating the candidate urine flow rate data has been described above, specific details will be omitted.

Here, the processed sound data used in the urine flow rate prediction part 1300 may be different from the data used in step S230 of classifying the urination sections and the non-urination sections. For example, the data used by the urine flow rate prediction part 1300 is data corresponding to each window when the sound data is divided into m windows so that consecutive windows overlap. The data used in step S230 of classifying the urination sections and the non-urination sections is data corresponding to each window when the sound data is divided into n windows so that consecutive windows do not overlap, wherein n may be smaller than m.

In step S260, the sound analysis system 1000 may obtain urination data. The sound analysis system 1000 may obtain the urination data by using the urination classification data obtained in step S230 of classifying the urination sections and the non-urination sections and the candidate urine flow rate data obtained in step S250 of predicting the urine flow rate.

As described above, in the method of analyzing the urination information, by determining whether a urination section exists prior to performing step S250 of predicting the urine flow rate, unnecessary analysis of the data may be prevented in advance when the urination-related sound is not reflected in the sound data to be analyzed.

Sound Analysis System Effect

Hereinafter, in the method of analyzing the urination information by using the sound analysis system 1000, practical effects in a case of performing the urination/non-urination classification process will be described.

Figure 18:
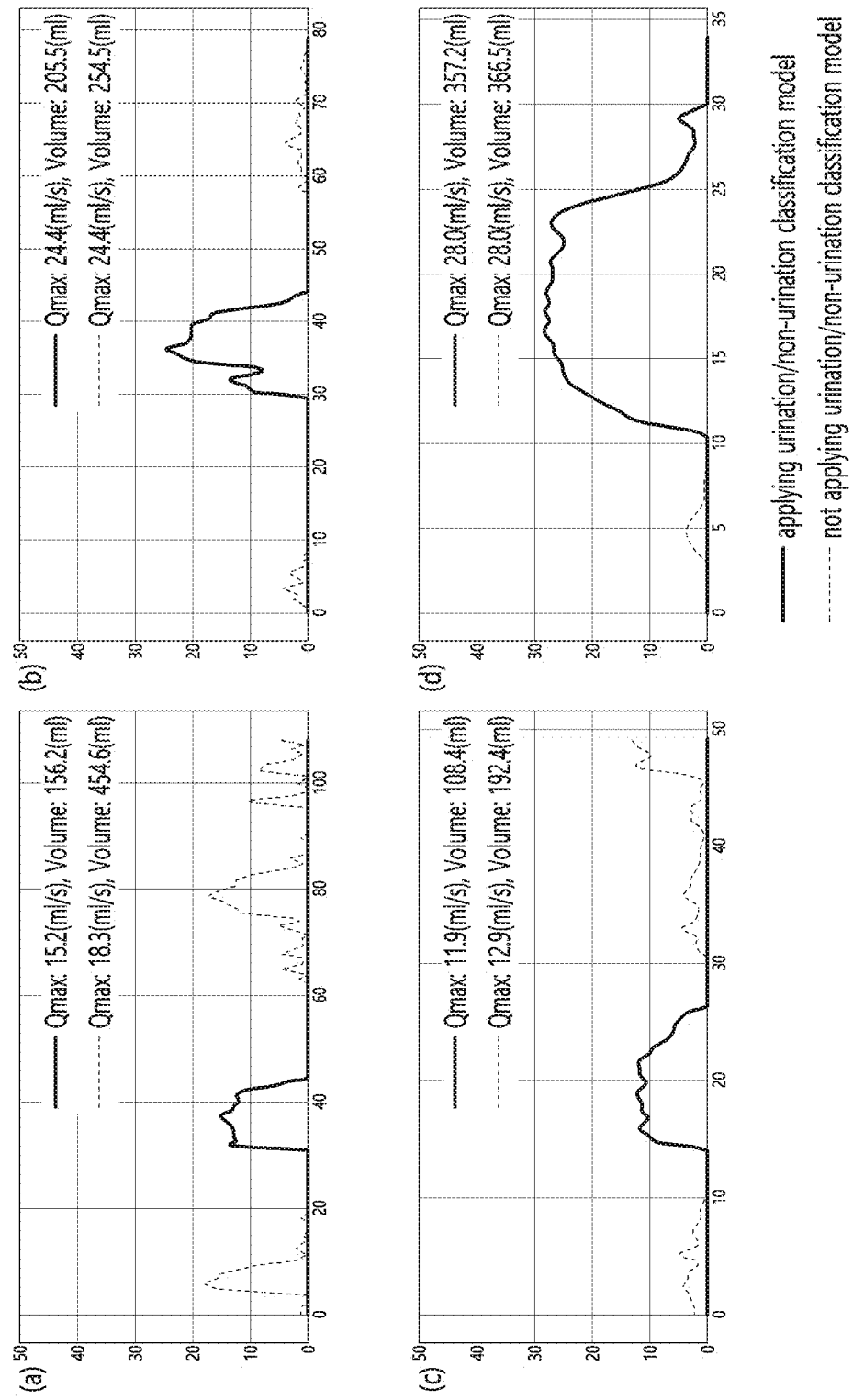
FIG. 18 is a view illustrating a graph for comparing a result of a case when the urination/non-urination classification model is not used and a result of a case when the urination/non-urination classification model is used according to the exemplary embodiment of the present specification.

FIG. 18 is a view illustrating a graph for comparing a result of a case when the urination/non-urination classification model is not used and a result of a case when the urination classification model is used according to the exemplary embodiment of the present specification.

In the method of analyzing the urination information, when the urination/non-urination classification model is not used, the urine volume may be excessively predicted compared to that of a case where the urination/non-urination classification model is used. For example, in FIG. 18(a) to FIG. 18(d), the urine volumes are measured to be larger in the case where the urination/non-urination classification model is not applied than in the case where the urination/non-urination classification model is applied. In particular, in the case of FIG. 18(a) and FIG. 18(c), it may be confirmed that differences between urine volumes in the case where the urination/non-urination classification model is applied and urine volumes in the case where the urination classification model is not applied are about twice as large.

In the method of analyzing the urination information, in the case when the urination/non-urination classification model is not used, the maximum urine flow rate may be excessively predicted compared to that of the case when the urination/non-urination classification model is used. For example, in FIG. 18(a) and FIG. 18(c), the maximum urine flow rate (Qmax) is measured to be larger when the urination/non-urination classification model is not applied than that of the case when the urination/non-urination classification model is applied. For men, since the maximum urine flow rate value is a significantly important factor in diagnosing a urination function, a non-excessive measurement of the maximum urine flow rate is an important issue.

In the method of analyzing the urination information, when the urination/non-urination classification model is not used, the accurate measurement of a urine flow time and a voiding time is more difficult than when the urination/non-urination classification model is used. For example, in FIGS. 18(a) and 18(c), it may be confirmed that when the urination/non-urination classification model is not applied, since there is a plurality of peak values, it is difficult to measure starting and ending points of urination and a resulting voiding time, whereas, when the urination/non-urination classification model is applied, since the starting and ending points of the urination are clear, the total voiding time may be accurately calculated.

As described above, it is absolutely essential to use the urination/non-urination classification model in order to accurately measure urination information such as a urine volume, a maximum urine flow rate, and a voiding time.

Model Training Method

Hereinafter, with reference to FIGS. 19 and 20, a process of training the urine flow rate prediction model and the urination/non-urination classification model described above will be described in detail.

Urine Flow Rate Prediction Model Training Method

Figure 19:
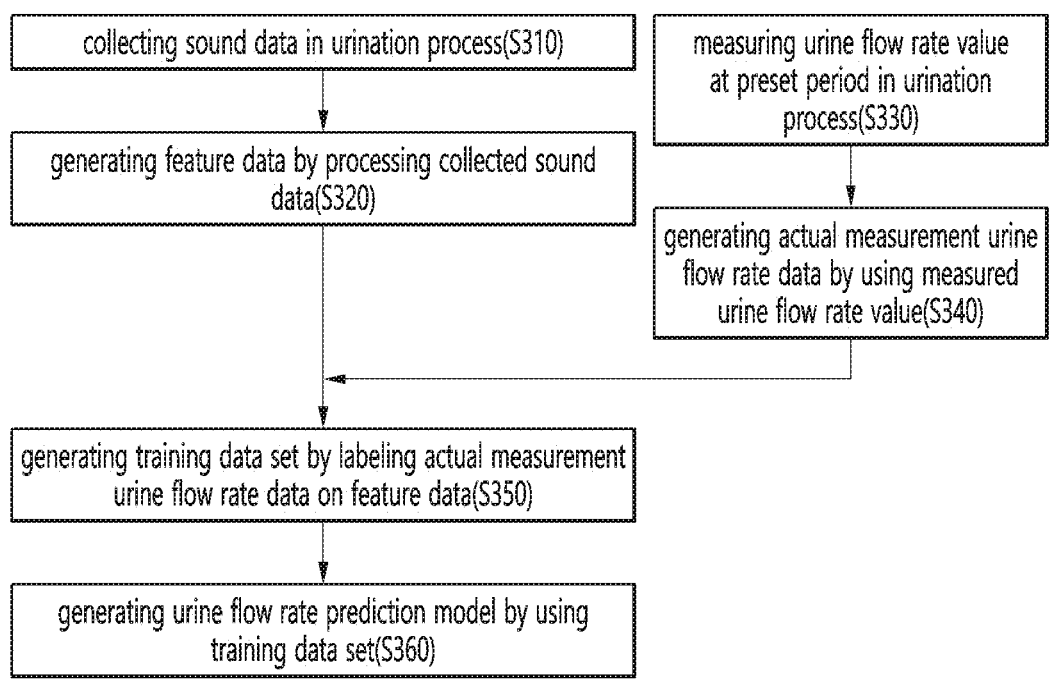
FIG. 19 is a flowchart illustrating a process of training the urine flow rate prediction model according to the exemplary embodiment of the present specification.

FIG. 19 is a flowchart illustrating a process of training the urine flow rate prediction model according to the exemplary embodiment of the present specification.

Referring to FIG. 19, a urine flow rate prediction model may include: step S310 of collecting sound data in a urination process; step S320 of generating feature data by processing the collected sound data; step S330 of measuring urine flow rate values at a preset period in the urination process; step S340 of generating actual measurement urine flow rate data by using the measured urine flow rate values; step S350 of generating a training data set by labeling the actual measurement urine flow rate data on the feature data; and step S360 of generating the urine flow rate prediction model by using the training data set.

Hereinafter, each step will be described. Each step of the method of training the urine flow rate prediction model may be performed by a person or a separate processor.

In step S310, sound data for a urination process may be collected in a process of training a urine flow rate prediction model. The sound data may be obtained by recording sound in the urination process of a person. Meanwhile, in step S310 of collecting the sound data, the sound data that does not include the sound in the urination process of the person may be collected in order to improve the performance of the urine flow rate prediction model. The above-described recording device 2000 may be used to collect the sound data.

In step S320, feature data may be generated from the sound data collected in the process of training the urine flow rate prediction model. The feature data may refer to data including feature values extracted from the sound data. Here, the feature values may include at least one of a spectrum time domain spectrum magnitude value, a frequency domain spectrum magnitude value, a frequency domain root mean square (RMS) value, a spectrogram magnitude value, a Mel-spectrogram magnitude value, a bispectrum score, a non-Gaussianity score, formants frequencies, a value of Log Energy, a zero crossing rate, a value of kurtosis, and a Mel-Frequency cepstral coefficient.

The feature data may be divided into a plurality of windows. For example, the feature data may include a plurality of segmented feature data respectively corresponding to the plurality of windows sequentially determined between a starting point and an ending point of the sound data or the feature data.

Since a process of generating the feature data and the segmented feature data is the same as the process of generating the target data and the segmented target data, specific details will be omitted.

In step S330, in the process of training the urine flow rate prediction model, urine flow rate values may be measured at a preset period for the urination process. For example, the urine flow rate values in the urination process may be measured by using a scale. For example, in the urination process, the urine flow rate values may be measured by using a toilet with a built-in scale or a toilet mounted on the scale. Specifically, as the urination process is performed through the toilet with the built-in scale or the toilet mounted on the scale, urine volumes over time may be measured by using changes over time of a weight measured on the scale, and urine flow rate values over time may be measured from data on the urine volumes. In this case, a period in which the urine flow rate values measured or a period in which the urine volumes are measured may correspond to the resolution of the sound data.

In step S340, actual measurement urine flow rate data may be generated by using the urine flow rate values measured in step S330 of measuring the urine flow rate. The actual measurement urine flow rate data may include urine flow rate values measured or calculated at a preset period.

The actual measurement urine flow rate data may be divided into a plurality of windows. For example, the actual measurement urine flow rate data may include a plurality of segmented actual measurement urine flow rate data respectively corresponding to the plurality of windows sequentially determined between a measurement starting time point and a measurement ending time point of the urination process. In this case, the size of a window dividing the actual measurement urine flow rate data may be the same as the size of the window dividing the above-described feature data. In addition, the number of segmented actual measurement urine flow rate data included in the actual measurement urine flow rate data may be the same as the number of segmented feature data included in the aforementioned feature data.

Steps S310 and S320 of collecting the above-described sound data and generating the feature data from the collected sound data may be performed at a previous time point or a later time point relative to steps S330 and S340 of measuring the urine flow rate values in the urination process and generating the actual measurement urine flow rate data by using the measured urine flow rate values, or may be performed in parallel.

In step S350, in the process of training the urine flow rate prediction model, the actual measurement urine flow rate data may be labeled on the feature data to generate a training data set. The feature data and the actual measurement urine flow rate data corresponding to each window section may be labeled with each other. For example, first training data may be generated by labeling first segmented feature data included in the feature data and configured to correspond to a first window section with first segmented actual measurement urine flow rate data included in the actual measurement urine flow rate data and configured to correspond to the first window section.

In step S360, the urine flow rate prediction model may be generated by using the aforementioned training data set. The urine flow rate prediction model may be trained by using the training data set. The trained urine flow rate prediction model may be used to obtain the segmented urine flow rate data by using the above-described segmented target data.

Urination/Non-Urination Classification Model Training Method

Figure 20:
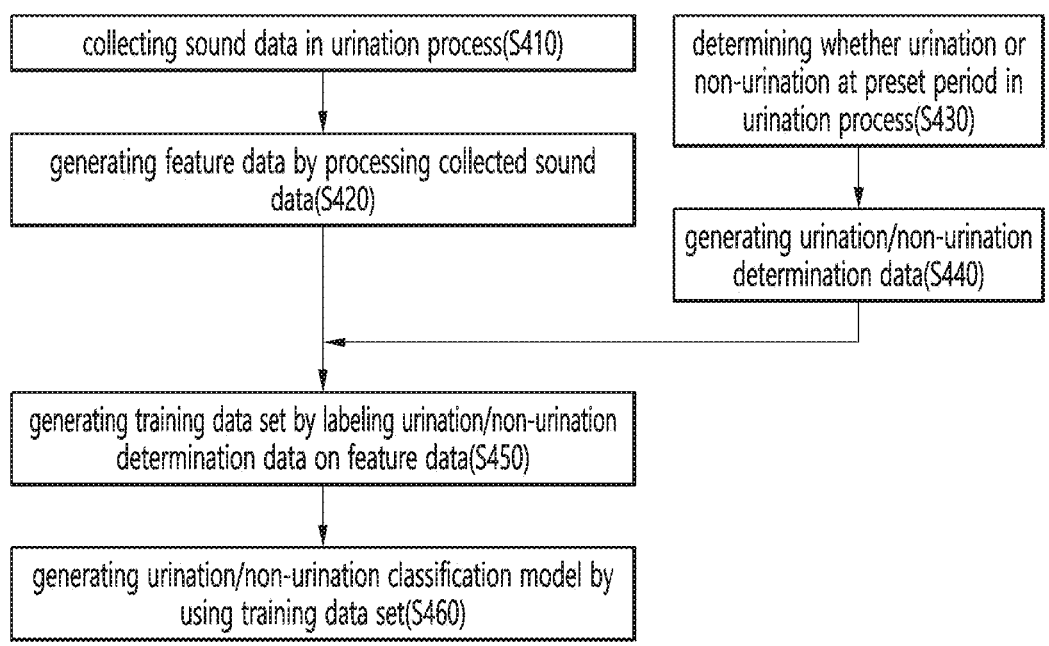
FIG. 20 is a flowchart illustrating a process of training the urination/non-urination classification model according to the exemplary embodiment of the present specification.

FIG. 20 is a flowchart illustrating a process of training the urination/non-urination classification model according to the exemplary embodiment of the present specification.

Referring to FIG. 20, the method of training urination/non-urination classification model may include: step S410 of collecting sound data in a urination process; step S420 of generating feature data by processing the collected sound data; step S430 of determining whether urination or non-urination at a preset period in the urination process; step S440 of generating urination/non-urination determination data; step S450 of generating a training data set by labeling urination/non-urination determination data on the feature data; and step S460 of generating a urination/non-urination classification model by using the training data set.

Hereinafter, each step will be described. Each step of the method of training urination/non-urination classification model may be performed by a person or a processor. Here, since step S410 of collecting the sound data and step S420 of generating the feature data by processing the collected sound data are respectively the same as steps S310 and S320 described in FIG. 19, specific details will be omitted.

In step S430, in a process of training the urination/non-urination classification model, whether urination or non-urination may be determined for the urination process. For example, a urination or non-urination section may be determined for the urination process by using the sound data recorded in the urination process. Specifically, the intensity in each time interval in the sound data recorded in the urination process may be compared with a predetermined value, so as to determine a corresponding section as a urination section or a non-urination section. For another example, a urination section and a non-urination section may be determined in the urination process by using urine volume data obtained by measuring urine volumes over time in each urination process. In measuring a urine volume for the urination process, the above-described method of measuring the urine volume may be used.

In step S440, urination/non-urination determination data may be generated by using the urination sections and the non-urination sections, which are determined in step S430 of determining whether urination or non-urination. The urination/non-urination determination data may include determination values determined at a preset period in the time domain.

The urination/non-urination determination data may be divided into a plurality of windows. For example, the urination/non-urination determination data may include a plurality of segmented determination data respectively corresponding to the plurality of windows sequentially determined between a measurement starting time point and a measurement ending time point of the urination process. In this case, the size of a window dividing the urination/non-urination determination data may be the same as the size of the window dividing the feature data generated in step S420. In addition, the number of segmented determination data included in the urination/non-urination determination data may be the same as the number of segmented feature data included in the feature data generated in step S420.

Steps S410 and S420 of collecting the above-described sound data and generating the feature data from the collected sound data may be performed at a previous time point or a later time point relative to steps S430 and S440 of determining whether urination or non-urination in the urination process and generating the determination data by using the determination values, or may be performed in parallel.

In step S450, in the process of training the urination/non-urination classification model, the urination/non-urination determination data may be labeled on the feature data to generate a training data set. The feature data and the urination/non-urination determination data respectively corresponding to each window section may be labeled with each other. For example, first training data may be generated by labeling the first segmented feature data included in the feature data and configured to correspond to a first window section with the segmented determination data included in the urination/non-urination determination data and configured to correspond to the first window section.

In step S460, a urination/non-urination classification model may be generated by using the above-described training data set. Specifically, the urination/non-urination classification model may be trained by using the training data set. The trained urination/non-urination classification model may be used to obtain the segmented classification data by using the above-described segmented target data.

Hereinafter, a method of correcting data, wherein urination data or urination information, which is obtained by using sound data, is corrected will be described. Here, note in advance that the urination data or the urination information, which is corrected by applying the method of correcting the data, may be urination data or urination information, which is not only obtained by the method of obtaining high accuracy urination information described through FIGS. 1 to 20 but also obtained by other methods.

In addition, in the following, for convenience of explanation, a case where urination data or urination information to be corrected is predicted values related to urine volumes is mainly described, but the technical idea of the present specification is not limited thereto, and a case of correcting predicted values for the above-described maximum urine flow rate, average urine flow rate, error time, or voiding time may be similarly applied thereto.

Method of Correcting Urination Data

Figure 21:
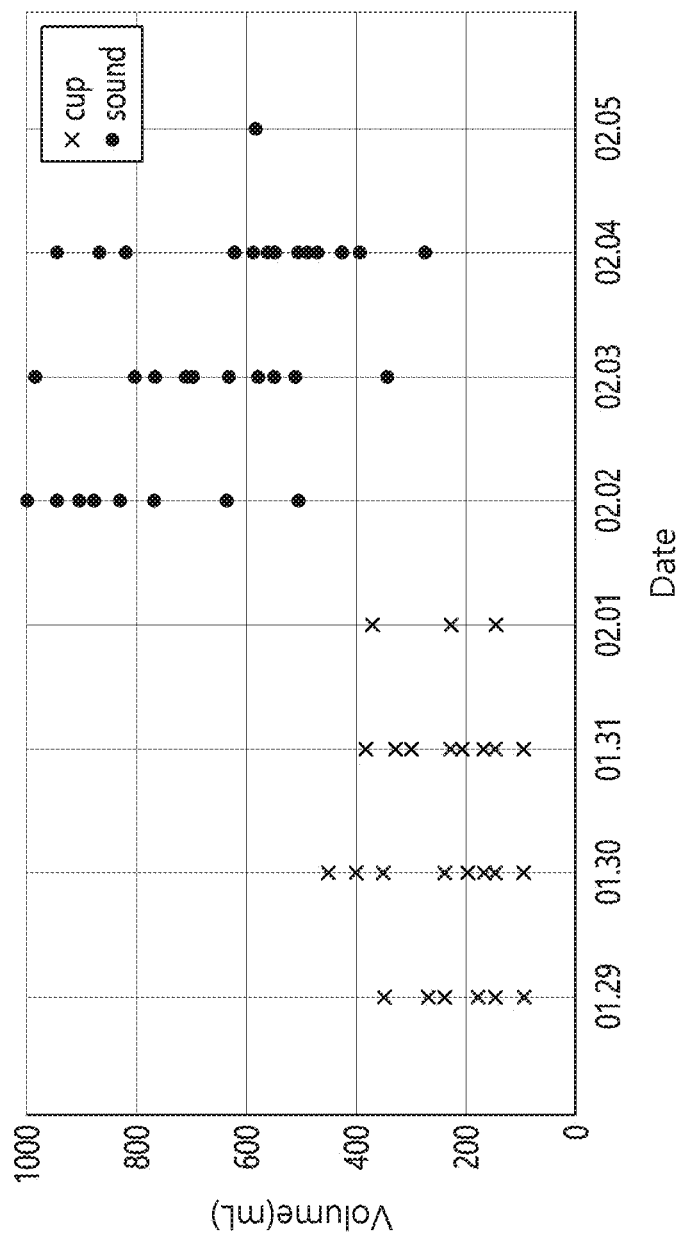
FIG. 21 is a view illustrating actual measurement data and prediction data according to the exemplary embodiment of the present specification.

FIG. 21 is a view illustrating actual measurement data and prediction data according to the exemplary embodiment of the present specification.

The actual measurement data may include urine volume measurement values measured in the urination process of any one individual (e.g., a general public, a patient, a subject, or the like) for a predetermined period of time. For example, the actual measurement data may include the urine volume measurement values measured in the urination process of one person during one day. As another example, the actual measurement data may include urine volume measurement values measured in the urination process of one person for a plurality of days. The urine volume measurement values may be obtained in various ways. For example, the urine volume measurement values may be obtained by using a measurement device such as a paper cup or a graduated cup, a portable household urine flow rate measurement device, a urine flow rate measurement device used in a medical institution, and a measurement device such as a scale.

The number of urine volume measurement values included in the actual measurement data may be the same as the number of urination processes of a corresponding individual.

The prediction data may include urine volume prediction values calculated in the urination process of any one individual for a predetermined period of time. For example, the prediction data may include urine volume prediction values obtained by using sound data obtained accordingly by recording sound in the urination process of a person during one day. As another example, the prediction data may include urine volume prediction values obtained by using sound data obtained accordingly by recording sound in the urination process of the person for a plurality of days. The urine volume prediction values may be obtained in various ways. For example, the urine volume prediction values may refer to values derived, from a process of estimating urine flow rates or urine volumes, by analyzing the sound data obtained by recording sound in the urination process of a person by any method. Specifically, the urine volume prediction values may be obtained by using the aforementioned sound analysis system 1000. In this case, the urine volume prediction values may be calculated from the candidate urine flow rate data obtained through the urine flow rate prediction part 1300 and the urination information extraction part 1500, or may be calculated from the urination data obtained through the urine flow rate prediction part 1300, the urination/non-urination classification part 1400, and the urination information extraction part 1500.

The number of urine volume prediction values included in the prediction measurement data may be the same as the number of urination processes of the corresponding individual.

Referring to FIG. 21, actual measurement data (marked with X) and prediction data (marked with ●) for the urination process of any one person for any period of time (e.g., from January 29 to February 5) are graphically shown, and the prediction data has a relatively large value when being compared with the actual measurement data. Specifically, the urine volume measurement values for the urination process from January 29 to February 1 are within about 100 ml to about 500 ml, whereas the urine volume prediction values for the urination process from February 2 to February 5 are within about 300 ml to about 1000 ml. In other words, when the urine volumes are predicted by using the sound data, the predicted values may have larger values than those of the actually measured urine volumes, and this needs to be corrected. Hereinafter, a case in which predicted urine volumes have larger values than actually measured urine volumes will be mainly described, but the technical idea of the present specification is not limited thereto, and may also be similarly applied to a case where the actually measured urine volumes have larger values than the predicted urine volumes.

Figure 22:
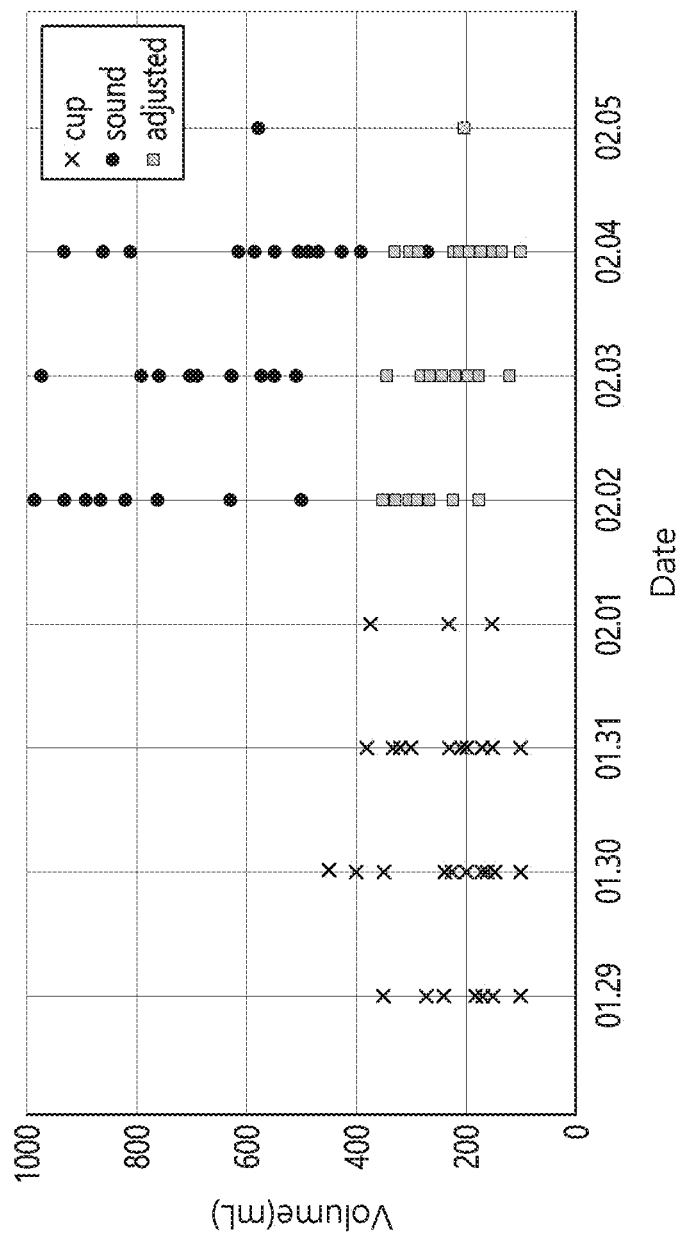
FIG. 22 is a view illustrating the actual measurement data, the prediction data, and corrected prediction data according to the exemplary embodiment of the present specification.

FIG. 22 is a view illustrating the actual measurement data, the prediction data, and corrected prediction data according to the exemplary embodiment of the present specification.

Referring to FIG. 22, corrected prediction data (marked with □) obtained by correcting prediction data is displayed in a graph shown in FIG. 21. Specifically, in FIG. 22, the corrected prediction values obtained by scaling the urine volume prediction values from February 2 to February 5 are displayed, and corrected prediction values may have values within about 100 ml to about 400 ml.

In general, a person's urine volume is proportional to the size of the bladder of a person, and even in different urination processes, each urine volume value may have a value within a certain range.

In consideration of such circumstances, prediction data for the urination process of the person may be corrected by using actual measurement data for the urination process of the person. For example, when the urine volume measurement values of the actual measurement data have a first range and the urine volume prediction values of the prediction data have a second range, the urine volume prediction values of the prediction data may be corrected such that the second range is the same as or similar to the first range.

Meanwhile, a range of values of the person's urine volume may be maintained within a certain period. In other words, since the person's urine volume may be determined depending on the size of the bladder of the person, the range of values of the person's urine volume may be maintained unless there is a circumstance such as a change in physical characteristics, a treatment, an occurrence of a disease, or the like.

Considering such a circumstance, on the basis of data at any one point in time, data at another point in time may be corrected for the urination-related data collected at different points in time. For example, current or future prediction data may also be corrected by using past actual measurement data, the current or future prediction data may also be corrected by using the past actual measurement data and past prediction data, and the reverse is also possible. Meanwhile, the urination-related data may be collected once more when there is a special circumstance described above, such as the change in physical characteristics, the treatment, or the occurrence of the disease.

Hereinafter, with reference to FIGS. 23 to 26, a method of correcting the prediction data for the urine volumes collected in the past or to be collected in the future by using the actual measurement data for the urine volumes previously collected will be described.

Figure 23:
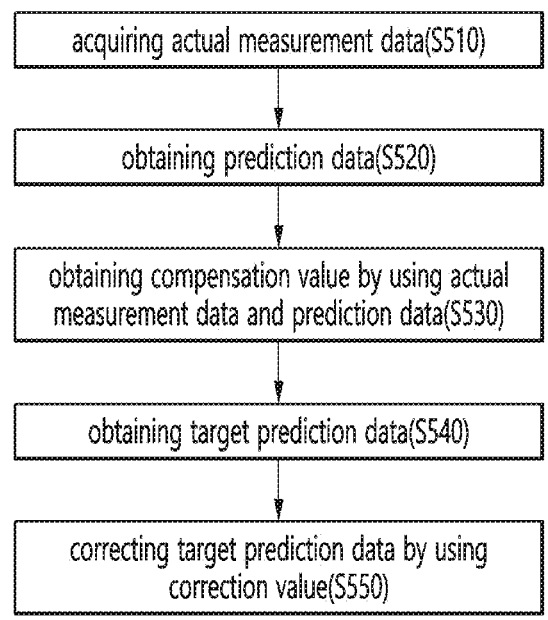
FIG. 23 is a flowchart illustrating a method of correcting data according to the exemplary embodiment of the present specification.

FIG. 23 is a flowchart illustrating a method of correcting data according to the exemplary embodiment of the present specification.

Referring to FIG. 23, the method of correcting the data may include: step S510 of obtaining actual measurement data; step S520 of obtaining prediction data; step S530 of obtaining a compensation value by using the actual measurement data and the prediction data; step S540 of obtaining target prediction data; and step S550 of correcting the target prediction data by using a correction value.

At least a part of each step in the method of correcting the data may be performed through the controller 1900 or a separate processor of the aforementioned sound analysis system 1000.

As an example, at least a part of the method of correcting the data may be performed by a data correction part. In hardware, the data correction part may be provided in a form of an electronic circuit that performs a control function by processing electrical signals, or in software, the data correction part may be provided in a form of a program or codes for driving a hardware circuit. The data correction part may receive data from the outside and perform the method of correcting the data by the received data, or on the received data.

Hereinafter, each step will be described in detail.

In step S510, in the method of correcting the data, actual measurement data may be obtained. As described above, the actual measurement data refers to data obtained by measuring urine volumes in the urination process of any one individual. Specifically, the actual measurement data may include a urine volume measurement value measured for each urination process of one person.

In step S510 of obtaining the actual measurement data, an actual measurement data group for a plurality of individuals may be obtained. For example, the above-described actual measurement data group may include first to s-th actual measurement data (where, s is a natural number greater than or equal to 2) for first to s-th individuals. Each actual measurement data may include at least one or more urine volume measurement values related to the urination process of the corresponding individual. As a result, obtaining of the actual measurement data group may be understood as collecting the urine volume measurement values measured in the urination process of the plurality of individuals.

In step S520, prediction data may be obtained in the method of correcting the data. As described above, the prediction data refers to data in which urine volumes are predicted in the urination process of any one individual. Specifically, the prediction data may include urine volume prediction values calculated by using the sound data recorded in the urination process of one person.

In step S520 of obtaining the prediction data, a prediction data group for a plurality of individuals may be obtained. For example, the prediction data group may include first to t-th prediction data (where, t is a natural number greater than or equal to 2, which may be the same as or different from s) for first to t-th individuals. Each prediction data may include at least one or more urine volume prediction values related to the urination process of a corresponding individual. As a result, obtaining of the prediction data group may be understood as collecting the urine volume prediction values calculated in the urination process of the plurality of individuals.

Step S510 of obtaining the actual measurement data and step S520 of obtaining the prediction data may be performed sequentially or in parallel.

In step S530, in the method of correcting the data, a compensation value may be obtained by using the actual measurement data and the prediction data. The compensation value may be understood as a value for correcting the collected prediction data or the prediction data to be collected later.

The compensation value may be calculated by applying a data analysis technique to both of the actual measurement data obtained in step S510 of obtaining the actual measurement data and the prediction data obtained in step S520 of obtaining the prediction data.

As an example, the compensation value may be calculated by using a descriptive statistical analysis technique. Specifically, the compensation value may be calculated by comparing a representative value of the actual measurement data (e.g., a mean value, a median value, a mode value, a variance value, and/or a standard deviation value for at least some of the urine volume measurement values) with a representative value of the prediction data (e.g., an average value, a median value, a mode value, a variance value, and/or a standard deviation value of at least some of the urine volume prediction values).

As another example, a compensation value may be calculated by using a regression analysis technique. Specifically, when using a value obtained from the actual measurement data as any one of an independent variable or a dependent variable, and when using a value obtained from the prediction data as the other of the independent variable or the dependent variable, a regression coefficient calculated through the regression analysis technique may be obtained as the compensation value. Here, simple liner regression, multilinear regression, logistic regression, ridge regression, lasso regression, polynomial regression, or non-linear regression may be selected as the regression analysis.

A compensation value may be obtained by using machine learning other than multi-dimensional scaling (MDS), principal component analysis (PCA), or regression analysis, in addition to the data analysis technique described above.

A compensation value may be calculated by using the actual measurement data group and the prediction data group. In other words, the compensation value may be calculated by using the actual measurement data and the prediction data for a single individual, or may be calculated by using the actual measurement data group and prediction data group for the plurality of individuals, that is, several people. A specific method of calculating the compensation value will be described later.

In step S540, in the method of correcting the data, target prediction data may be obtained. The target prediction data may refer to data to be corrected by using the above-described compensation value. For example, the target prediction data may refer to urine volume prediction values calculated from the sound data obtained before or obtained newly after a data collection period during which the prediction data or the actual measurement data, which are used to calculate the compensation value, are obtained. Naturally, prediction data or urine volume prediction values, which are used to obtain the compensation value, may be target prediction data.

The target prediction data to be corrected may be prediction data for an arbitrary individual. For example, when a prediction data group and an actual measurement data group, which are used to calculate a correction value, include at least of first actual measurement data and first prediction data for a first individual and second actual measurement data and second prediction data for a second individual, the target data to be corrected may include the prediction data or the urine volume to measurement values for the first and second individuals as well as a third individual different from the first and second individuals. In other words, the aforementioned correction value is not limited to and applied only to the prediction data of a specific individual involved in calculating the correction value, but may also be used to correct the prediction data of an individual not involved in the calculating of the correction value.

In step S550, in the method of correcting the data, the target prediction data may be corrected by using the correction value. For example, a corrected urine volume prediction value may be generated by multiplying the target urine volume prediction value of the target prediction data and the correction value.

Hereinafter, the method of correcting the data will be described in detail with reference to FIGS. 24 to 26.

Figure 24:
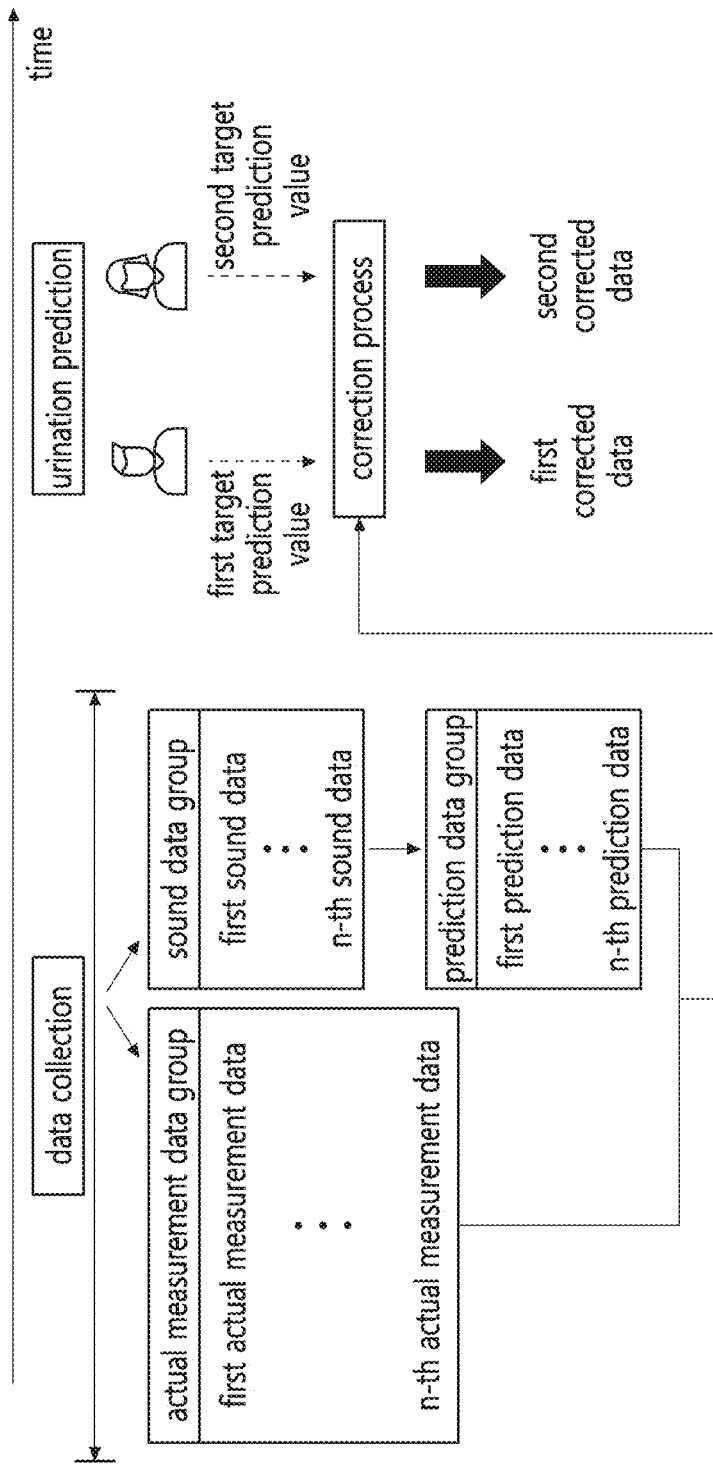
FIG. 24 is a view illustrating a process of correcting the data according to the exemplary embodiment of the present specification.

FIG. 24 is a view illustrating a process of correcting the data according to the exemplary embodiment of the present specification.

Figure 25:
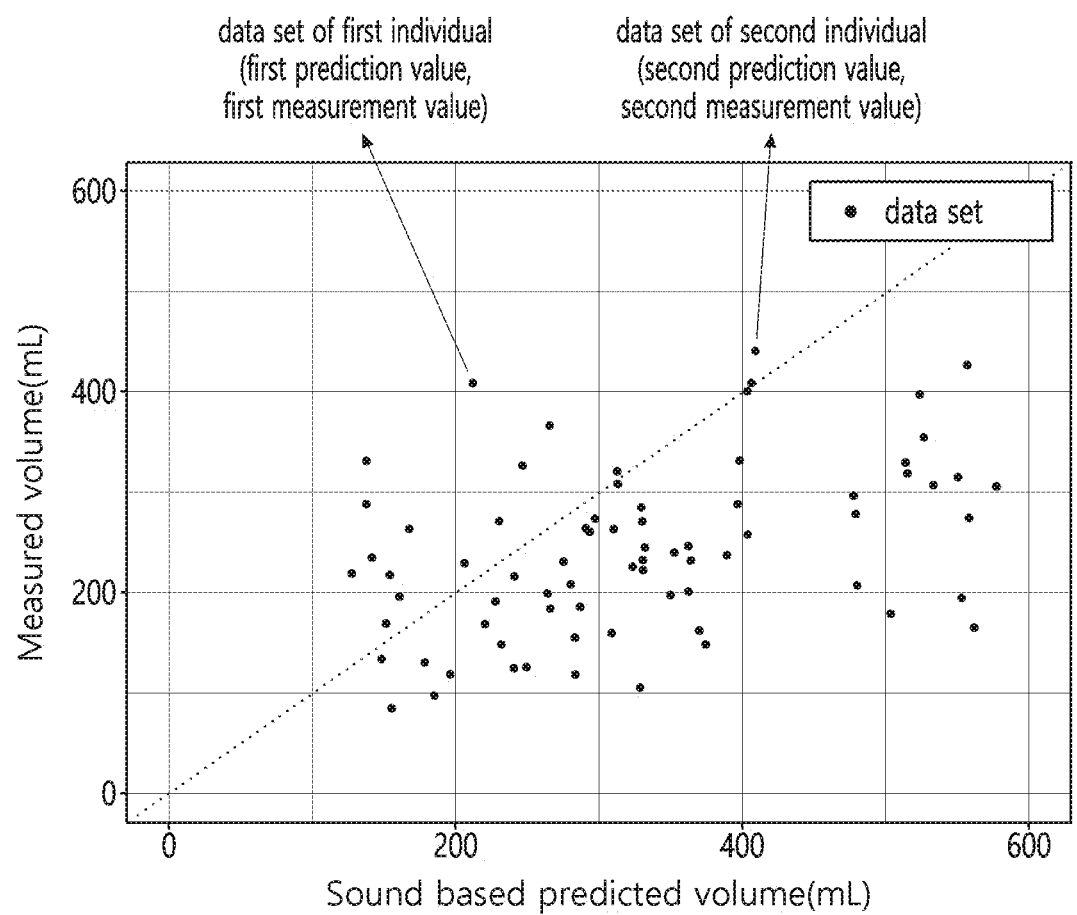
FIG. 25 is a graph illustrating a relationship between the actual measurement data and the prediction data before data correction according to the exemplary embodiment of the present specification.

FIG. 25 is a graph illustrating a relationship between the actual measurement data and the prediction data before data correction according to the exemplary embodiment of the present specification.

Figure 26:
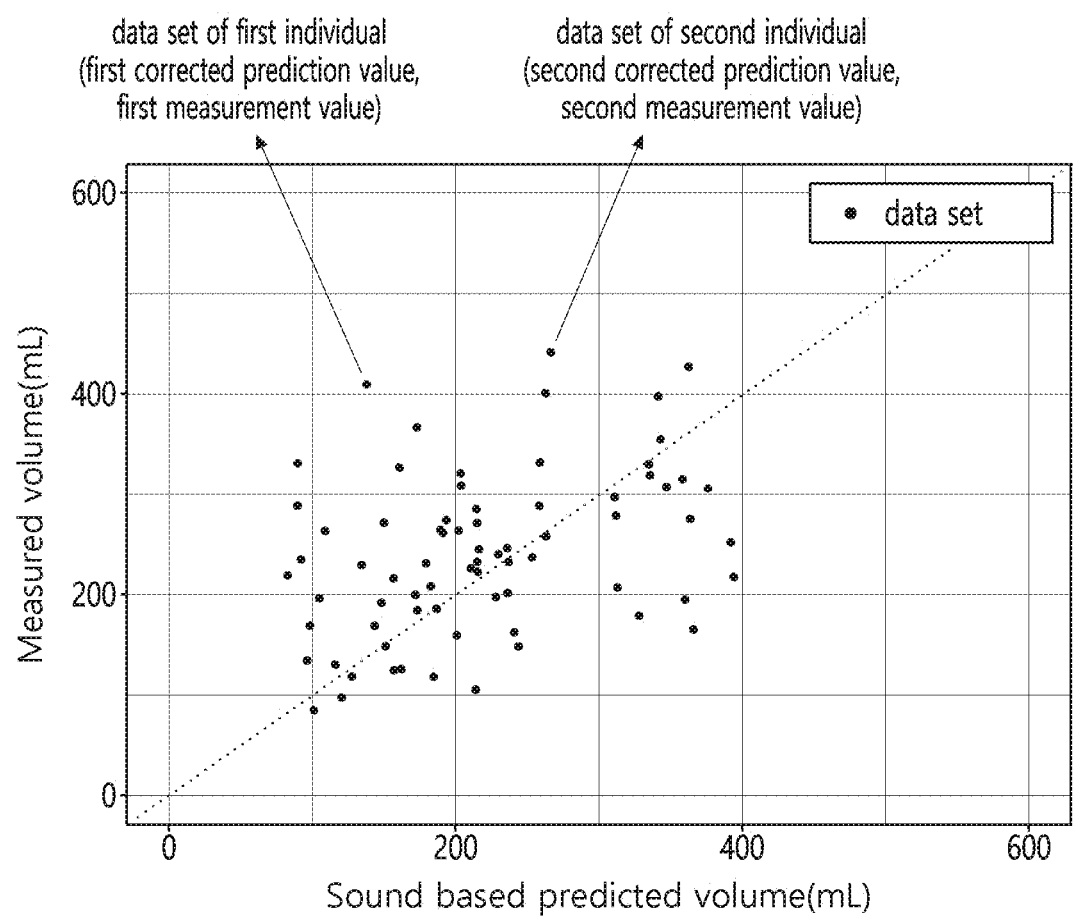
FIG. 26 is a graph illustrating a relationship between the actual measurement data and the prediction data after the data correction according to the exemplary embodiment of the present specification.

FIG. 26 is a graph illustrating a relationship between the actual measurement data and the prediction data after the data correction according to the exemplary embodiment of the present specification.

Referring to FIG. 24, urine volume prediction for a target person may be performed by using data collected during a data collection period.

In the data collection period, an actual measurement data group may be obtained. The actual measurement data group is data for a plurality of individuals, and may refer to a set of actual measurement data for each individual. For example, the actual measurement data group may include first to s-th actual measurement data for first to s-th individuals.

A sound data group may be obtained in the data collection period. The sound data group is data for the plurality of individuals, and may refer to a set of sound data for each individual. For example, the sound data group may include first to t-th sound data for first to t-th individuals. Sound data for each individual may be understood as sound data recorded in the urination process during the data collection period of each individual, and may refer to data obtained by recording sound during a single urination process or a plurality of urination processes.

A prediction data group may be obtained in the data collection period. The prediction data group is data for the plurality of individuals, and may refer to a set of prediction data for each individual. For example, the prediction data group may include first to t-th prediction data for first to t-th individuals.

The prediction data group may be calculated from the sound data group. For example, first prediction data for a first individual may be calculated from first sound data for the first individual. The first prediction data may include at least one or more urine volume prediction values, and the number of urine volume prediction values included in the first prediction data may correspond to the number of urination processes reflected in first sound data. The first to t-th individuals related to the prediction data group may include the first to s-th individuals related to the actual measurement data group.

The data collection period may be a short period of time in hours or days, or a long period of time in months or years. For example, the data collection period may be 6 hours, 12 hours, 18 hours, 1 day, 4 days, 7 days, 10 days, 14 days, 1 month, 3 months, 6 months, or 1 year.

A data set group may be generated from the actual measurement data group and the prediction data group prior to calculating a correction value.

The data set group may include a plurality of data sets. For example, the data set group may include a data set for each of the plurality of individuals.

The data set may be generated from the actual measurement data in the actual measurement data group and the prediction data in the prediction data group. The data set may include values related to the measurement of urine volumes and values related to the prediction of the urine volumes. For example, a first data set included in the data set group is generated from first actual measurement data and first prediction data, and specifically, may be generated by associating a representative measurement value that is a representative value of urine volume prediction values included in the first actual measurement data and a representative prediction value that is a representative value of the urine volume prediction values included in the first prediction data. In this case, the representative measurement value may be a sum value, an average value, a median value, a mode value, a variance value, or a standard deviation value of the urine volume measurement values included in the actual measurement data, and the representative prediction value may be a sum value, an average value, a median value, a mode value, a variance value, or a standard deviation value of the urine volume prediction values included in the prediction data.

In other words, the data set may be understood as a concept in which at least some of the actual measurement data and prediction data for any one individual are expressed as one set. Accordingly, for one individual, one data set may be generated, or a plurality of data sets may be generated.

As an example, when a data set group is generated from an actual measurement data group and a prediction data group, which are collected for a plurality of individuals during one day, the data set group may include one data set per individual when a data set includes an average measurement value for one day and an average prediction value for one day.

As another example, when a data set group is generated from an actual measurement data group and a prediction data group, which are collected for a plurality of individuals for four days, and four data sets may be generated per individual when a data set includes an average measurement value for one day and an average prediction value for one day.

The process of generating the data set is not limited to the above-described example. The data set may be generated for each of the plurality of urination processes occurring on the same day, and one data set may be generated for all urination processes occurring over a plurality of days for each individual.

The data set may be expressed in various forms. For example, as shown in FIGS. 25 and 26, the data set may be displayed in a form of coordinates on a graph.

A correction value may be calculated from a data set group by using the correction process.

As an example, a regression analysis technique may be used in calculating a correction value. Referring to FIG. 25, a data set group may include a data set of which the average of urine volume prediction values for each individual is an independent variable and the average of urine volume measurement values for each individual is a dependent variable, and thus a function representing a relationship between the urine volume prediction value and the urine volume measurement value may be obtained by using the data set group. In this case, the obtained function may be a linear function, and a slope thereof may be obtained as the correction value. In addition, a point at which the urine volume prediction value has a larger value than the urine volume measurement value, the slope at the point may have a value between 0 and 1.

Target prediction data for a target individual may be corrected by using the calculated correction value. The target individual may refer to an individual for which urination information is to be obtained. The target prediction data may refer to prediction data regarding the urination process of the target individual. For example, a first target prediction value may be calculated from sound data obtained by recording sound in the urination process of a first target individual, and first corrected data may be obtained by applying the correction value to the first target prediction value. Likewise, a second target prediction value may be calculated from sound data obtained by recording sound in the urination process of a second target individual, and second corrected data may be obtained by applying the correction value to the second target prediction value.

The target prediction data may be obtained after the data collection period, and the prediction data obtained during the data collection period may also be the target prediction data.

By using the correction value, the target prediction data may be corrected to be in a range similar to that of the measurement values. Referring to FIGS. 25 and 26, in FIG. 25, in data sets of more than half of the data set group before correction, the urine volume prediction values have larger values than the urine volume measurement values so as to be positioned far from a direct proportional reference line, whereas in FIG. 26, most data sets in the data set group after the correction may be positioned adjacent to the direct proportional reference line.

In the above, the process of calculating the correction value by using the actual measurement data group and the prediction data group for the plurality of individuals has been described, but the technical idea of the present specification is not limited thereto, and the prediction data may also be corrected by using only the actual measurement data for one individual.

As an example, actual measurement data may be collected for a target individual during a data collection period, statistical values of the collected actual measurement data may be calculated, and prediction data for the target individual may be corrected on the basis of the calculated statistical values.

Here, the statistical values of the actual measurement data may be at least one of a mode value, a median value, an average value, a variance value, or a standard deviation value of the urine volume measurement values measured in the urination process of the target individual during the data collection period.

The prediction data for the target individual may be corrected by correcting the urine volume to prediction values, so as to correspond the statistical values of the urine volume prediction values included in the prediction data for the target individual to the statistical values of the actual measurement data for the target individual.

Meanwhile, the prediction data for the target individual to be the target for correction may be data calculated from the sound data on the urination process of the target individual and obtained before the data collection period, during the data collection period, or after the data collection period.

Through the method of correcting the data described above, the correction of the prediction data for the urination process may be performed by using the actual measurement data for the urination process, or performed by using the actual measurement data and the prediction data for the urination process. In such a correction process, when the collection of actual measurement data is easy, for example, when measuring a urine volume in the urination process by using a paper cup, it may be said that usefulness of the present disclosure is significantly large in that the correction value is easily calculated and the corrected prediction data may secure a certain level of accuracy.

In the above, features, structures, effects, etc. described in the above exemplary embodiments are included in at least one embodiment of the present disclosure, and are not necessarily limited to only one embodiment. Furthermore, the features, structures, effects, etc. illustrated in each embodiment may be implementable by way of combinations or modifications for other embodiments by those skilled in the art to which the embodiments belong. Accordingly, the contents related to such combinations and modifications should be interpreted as being included in the scope of the present specification.

In addition, in the above, the present disclosure has been described focusing on the embodiments, but these are only examples and do not limit the technical idea of the present specification, and thus those skilled in the art to which this specification pertains will appreciate that various modifications and applications not exemplified above are possible without departing from the essential characteristics of the present embodiments. That is, each component specifically shown in the embodiments may be implemented by modifications. In addition, differences related to such modifications and applications should be construed as being included in the scope of the present specification defined in the appended claims.

The invention claimed is:

1. A method of obtaining urination information, the method comprising:
  obtaining sound data by using a sound sensor;
  obtaining, by a processor, a first plurality of segmented target data corresponding to a first plurality of windows from the sound data, wherein each of the first plurality of windows includes a first length and is sequentially determined between a starting point and an ending point of the sound data;

obtaining, by the processor, a second plurality of segmented target data corresponding to a second plurality of windows from the sound data, wherein each of the second plurality of windows includes a second length and is sequentially determined between the starting point and the ending point of the sound data;

obtaining, by the processor, a plurality of segmented classification data by sequentially inputting the first plurality of segmented data into a classification model, wherein the classification model is configured to output data comprising at least a value for classifying a urination section or a non-urination section when data related to urination sound are inputted;

obtaining, by the processor, a plurality of segmented urine flow rate data by sequentially inputting the second plurality of segmented data into a prediction model, wherein the prediction model is configured to output data comprising at least a value for urine flow rate when data related to urination sound are inputted; and obtaining urination data using at least the plurality of segmented classification data and the plurality of segmented urine flow rate data.

2. The method of claim 1,
wherein the first plurality of segmented target data includes first to m-th segmented target data and the first plurality of windows includes m windows,
wherein the first to m-th segmented target data corresponds to the m windows,
wherein the m is a natural number greater than or equal to 2,
wherein the second plurality of segmented target data includes first to n-th segmented target data and the second plurality of windows includes n windows,
wherein the first to n-th segmented target data corresponds to the n windows, and
wherein the n is a natural number greater than or equal to 2.

3. The method of claim 2, wherein consecutive windows among the n windows partially overlap each other.

4. The method of claim 3,
wherein consecutive windows among the m windows partially overlap each other, and
wherein an overlapping degree of the consecutive windows among the m windows is different from an overlapping degree of consecutive windows among the n windows.

5. The method of claim 3,
wherein consecutive windows among the n windows partially overlap each other, and
wherein an overlapping degree of the consecutive windows among the m windows is same as an overlapping degree of consecutive windows among the n windows.

6. The method of claim 2, wherein consecutive windows among the m windows do not overlap each other.

7. The method of claim 2, wherein the each of m windows are same as each of the n windows.

8. The method of claim 2, wherein the obtaining of the first plurality of segmented target data comprises:
transforming the sound data to spectrogram data; and
obtaining the first to m-th segmented target data corresponding to the m windows from the spectrogram data.

9. The method of claim 2,
wherein the obtaining of the first plurality of segmented target data comprises:
obtaining first to m-th segmented sound data corresponding to the m windows, and transforming each of the first to m-th segmented sound data to spectrogram data to obtain the first to m-th segmented target data.

10. The method of claim 1, wherein the obtaining of the urination data comprises:
obtaining urination classification data using the plurality of segmented classification data;
obtaining candidate urine flow rate data using the plurality of segmented urine flow rate data; and
processing the candidate urine flow rate data using the urination classification data.

11. The method of claim 10, wherein the urination data are obtained through convolution operating of the urination classification data and the candidate urine flow rate data.

12. The method of claim 10, wherein the urination data are obtained through multiple operating of at least part of the urination classification data and the candidate urine flow rate data.

13. The method of claim 1, further comprising:
correcting the urination data by using a compensation value.

14. The method of claim 13, wherein the compensation value is obtained by:
obtaining sample sound data including sound of urination,
obtaining a predictive value by using the sample sound data, the classification model, and the prediction model, wherein the predictive value represents voiding volume,
obtaining a measured value by measuring voiding volume corresponding to the sample sound data, and
obtaining the compensation value by using at least the predictive value and the measured value.

15. A non-transitory computer-readable recording medium having recorded thereon one or more computer readable instructions which, when executed by at least one processor of an electronic device, cause the electronic device to perform operations comprising:
obtain sound data recorded by a sound sensor;
obtain, by the at least one processor, a first plurality of segmented target data corresponding to a first plurality of windows from the sound data, wherein each of the first plurality of windows has a first length and is sequentially determined between a starting point and an ending point of the sound data;
obtain, by the at least one processor, a second plurality of segmented target data corresponding to a second plurality of windows from the sound data, wherein each of the second plurality of windows has a second length and is sequentially determined between the starting point and the ending point of the sound data;
obtain, by the at least one processor, a plurality of segmented classification data by sequentially inputting the first plurality of segmented data into a classification model, wherein the classification model is configured to output data comprising at least a value for classifying a urination section or a non-urination section when data related to urination sound are inputted;
obtain, by the at least one processor, a plurality of segmented urine flow rate data by sequentially inputting the second plurality of segmented data into a prediction model, wherein the prediction model is configured to output data comprising at least a value for urine flow rate when data related to urination sound are inputted; and
obtain urination data using at least the plurality of segmented classification data and the plurality of segmented urine flow rate data.

16. The method of claim 1, wherein the first length is same as the second length.

17. The method of claim 2, wherein the first length is different from the second length.

* * * * *